US010435717B2

(12) United States Patent
Keasling et al.

(10) Patent No.: US 10,435,717 B2
(45) Date of Patent: *Oct. 8, 2019

(54) GENETICALLY MODIFIED HOST CELLS AND USE OF SAME FOR PRODUCING ISOPRENOID COMPOUNDS

(71) Applicant: The Regents of the University of California, Oakland, CA (US)

(72) Inventors: Jay D. Keasling, Berkeley, CA (US); James Kirby, Berkeley, CA (US); Eric M. Paradise, Vienna, VA (US)

(73) Assignee: The Regents of the University of California, Oakland, CA (US)

( * ) Notice: Subject to any disclaimer, the term of this patent is extended or adjusted under 35 U.S.C. 154(b) by 12 days.

This patent is subject to a terminal disclaimer.

(21) Appl. No.: 15/722,844

(22) Filed: Oct. 2, 2017

(65) Prior Publication Data
US 2018/0030481 A1 Feb. 1, 2018

Related U.S. Application Data

(63) Continuation of application No. 14/451,056, filed on Aug. 4, 2014, now Pat. No. 9,809,829, which is a continuation of application No. 11/571,315, filed as application No. PCT/US2005/026190 on Jul. 21, 2005, now Pat. No. 8,828,684.

(60) Provisional application No. 60/592,009, filed on Jul. 27, 2004.

(51) Int. Cl.
*C12P 5/00* (2006.01)
*C12N 9/10* (2006.01)
*C12N 15/81* (2006.01)
*C12P 23/00* (2006.01)
*C12N 9/04* (2006.01)
*C12N 9/88* (2006.01)

(52) U.S. Cl.
CPC ............ *C12P 5/007* (2013.01); *C12N 9/0006* (2013.01); *C12N 9/1085* (2013.01); *C12N 9/88* (2013.01); *C12N 15/81* (2013.01); *C12P 23/00* (2013.01); *C12Y 101/01034* (2013.01); *C12Y 205/01092* (2013.01); *C12Y 402/03024* (2013.01)

(58) Field of Classification Search
None
See application file for complete search history.

(56) References Cited

U.S. PATENT DOCUMENTS

| 5,460,949 | A | 10/1995 | Saunders et al. | |
| 6,531,303 | B1 | 3/2003 | Millis et al. | |
| 6,689,593 | B2 | 2/2004 | Millis et al. | |
| 7,091,027 | B1* | 8/2006 | Wallaart | C12N 9/88 |
| | | | | 435/232 |
| 7,129,392 | B2 | 10/2006 | Hahn et al. | |
| 7,172,886 | B2 | 2/2007 | Keasling et al. | |
| 7,192,751 | B2 | 3/2007 | Keasling et al. | |
| 7,229,784 | B2 | 6/2007 | Holtzman et al. | |
| 7,238,574 | B1 | 7/2007 | Matsuda et al. | |
| 8,759,632 | B2 | 6/2014 | Ro et al. | |
| 2002/0106772 | A1 | 8/2002 | Croteau et al. | |
| 2003/0148479 | A1 | 4/2003 | Keasling et al. | |
| 2003/0092144 | A1* | 5/2003 | Millis | C07C 403/08 |
| | | | | 435/157 |
| 2004/0029239 | A1 | 2/2004 | Ohto et al. | |
| 2004/0063182 | A1 | 4/2004 | Ohto et al. | |
| 2004/0110259 | A1 | 6/2004 | Baugh et al. | |

FOREIGN PATENT DOCUMENTS

| CA | 2433534 | 7/2002 |
| EP | 0982404 | 1/2000 |
| EP | 1345955 | 10/2003 |
| EP | 1345956 | 10/2003 |
| WO | WO 00/01650 | 1/2000 |
| WO | WO 2000/12725 | 3/2000 |
| WO | WO 2002/03981 | 1/2002 |
| WO | WO 2004/011667 | 2/2004 |

OTHER PUBLICATIONS

Mao et al in "MET3 Promoter: A Tightly Regulated Promoter and Its Application in Construction of Conditional Lethal Strain" (Current Microbiology, vol., 45, 2002, pp. 37-40; IDS reference). (Year: 2002).*
Brock et al. "On the mechanism of the antifungal agent propionate Propionyl-CoA inhibits glucose metabolism in Aspergillus nidulans" (2004) Eur J. Biochem. 271:3227-3241.
Choi et al. "Highl-Level Production of Poly(3-Hydroxybutyrate-co-3-Hydroxyvalerate) by Fed-Batch Culture of Recombinant *Escherichia coli*" (1999) Appl. Environ. Microbio. 65:4363-4368.
Donald et al., "Effects of Overproduction of the Catalytic domain of 3-Hydroxy-3-Methyglutaryl Coenzyme A Reductase on Squalene Synthesis in *Saccharomyces cerevisiae*" (1997) Appl. Env. Microbiol. 63:3341-3344.
Gardner and Hampton, "A Highly Conserved Signal Controls Degradation of 3-Hydroxy-3-methylglutaryl-coenzyme A (HMG-CoA) Reductase in Eukaryotes", J. Biol. Chem., 1999, 274(44):31671-31678.

(Continued)

*Primary Examiner* — Catherine S Hibbert
(74) *Attorney, Agent, or Firm* — Bozicevic Field & Francis, LLP; Paula A. Borden

(57) ABSTRACT

The present invention provides genetically modified eukaryotic host cells that produce isoprenoid precursors or isoprenoid compounds. A subject genetically modified host cell comprises increased activity levels of one or more of mevalonate pathway enzymes, increased levels of prenyltransferase activity, and decreased levels of squalene synthase activity. Methods are provided for the production of an isoprenoid compound or an isoprenoid precursor in a subject genetically modified eukaryotic host cell. The methods generally involve culturing a subject genetically modified host cell under conditions that promote production of high levels of an isoprenoid or isoprenoid precursor compound.

21 Claims, 8 Drawing Sheets

Specification includes a Sequence Listing.

(56) References Cited

OTHER PUBLICATIONS

Gardner et al., "An Oxysterol-derived Positive Signal for 3-Hydroxy-3-methylglutaryl-CoA Reductase Degradation in Yeast", J. Biol. Chem., 2001, 276(12):8681-8694.
Grabowska; et al., "Effect of squalene synthase gene disruption on synthesis of polyprenols in *Saccharomyces cerevisiae*", FEBS Lett, 1998, 434(3):406-408.
Hamano et al. "Cloning of a Gene Cluster Encoding Enzymes Responsible for the Mevalonate Pathway from a Terpenoid-antibiotic-producing *Streptomyces* Strain" (2001) Biosci. Biotechnol. Biochem. 65:1627-1635.
Hart, "Metabolic Engineering of *Saccharomyces cerevisiae* Towards Increased Production of Terpenes and Characterization of Sterol Biosynthetic Enzymes", Ph.D. thesis, UMI, 2001, p. 1-144, UMI No. 3021132.
Jackson et al. "Metabolic Engineering to Produce Sesquiterpenes in Yeast" (2003) Organ. Lett. 5:1629-1632.
Jackson., "Yeast as a host for sesquiterpene production", Doctoral Thesis. Rice University (Nov. 2004).
Kontoyiannis, et al. "Overexpression of Erg11 by the regulatable GAL1 promoter confers azole resistance in *Saccharomyces cerevisiae*". Abstract of the Interscience Conference on Antimicrobial Agents and Chemotherapy, 1999, 39:586, XP009089312.
T. Kuzuyama. "Heterologous Mevalonate Production in *Streptomyces lividans* TK23" (2004) Biosci. Biotechnol. Biochem. 68(4): 931-934.
Loza-Tavera, "Monoterpenes in Essential Oils. Biosynthesis and Properties", Advances in Experimental Medicine and Biology, 1999, 464:49-62.
Martin et al. "Engineering a mevalonate pathway in *Escherichia coli* for production of terpenoids" (2003) Nat. Biotech. 21(7):796-802.
Mao et al., "MET3 Promoter: A Tightly Regulated Promoter and Its Application in Construction of Conditional Lethal Strain", Current Micriobiology, 2002, 45:37-40.
Murli et al."Metabolic engineering of *Escherichia coli* for improved 6-deoxyerythronolide B production" (2003) J. Ind. Microbiol. Biotechnol. 30: 500-509.
Parke et al., "Toxicity Caused by Hydroxycinnamoyl-Coenzyme A Thioester Accumulation in Mutants of *Acinetobacter* sp. Strain ADP1" (2004) Appl. Environ. Microbio. 70: 2974-2983.
Polakowski et al. "Overexpression of a cytosolic hydroxymethlglutaryl-CoA reductase leads to squalene accumulation in yeast" (1998) Appl. Microbiol. Biotechnol. 49: 66-71.
Shianna et al., "Identification of a UPC2 Homolog in *Saccharomyces cerevisiae* and Its Involvement in Aerobic Sterol Uptake", Journal of Bacteriology, 2001, 183(3):830-834.
Shimada et al., "Increased Carotenoid Production by the Food Yeast Candida utilis through Metabolic Engineering of the Isoprenoid Pathway", Applied and Environmental Microbiology, 1998, 64(7):2676-2680.
Subrahmanyam et al. "Overproduction of a Functional Fatty Acid Biosynthetic Enzyme Blocks Fatty Acid Synthesis in *Escherichia coli*" (1998) J. Bact. 180: 4596-4602.
Szkopinska et al. "The regulation of activity of main mevalonic acid pathway enzymes: Farnesyl disphosphate synthase, 3-hydroxy-3-methylglutaryl-CoA reductase, and squalene synthase in yeast *Saccharomyces cerevisiae*" Biochemical and Biophysical Research Communications, 2000, 267(1):473-477, XP002450431.
K. Tabata. "Production of mevalonate by a metabolically-engineered *Escherichia coli*" (2004) Biotechnology Letters. 26: 1487-1491.
Vik et al., "Upc2p and Ecm22p, Dual Regulators of Sterol Biosynthesis in *Saccharomyces cerevisiae*", Molecular and Cellular Biology, 2001, 21(19):6395-6405.
Wang et al., "Functional Characterization of Genes Involved in Isoprenoid Biosynthesis from Aspergillus Nidulans Using Metabolic-Engineered *E. Coli*", Abstracts of the General Meeting of the American Society for Microbiology, 2002, 102:235.
Wang et al., "Potential use of a Novel Geranylgeranyl Diphosphate Synthase Gene from Aspergillus Nidulans in Metabolic Engineering of Isoprenoid Production", Abstracts of the General Meeting of the American Society for Microbiology, 2002, 102(23):235.
Wentzinger et al. "Inhibition of squalene synthase and squalene epoxidase in tobacco cells triggers an up-regulation of 3-hydroxy-3-methylglutaryl coenzyme A reductase" Plant Physiology, 2002, 130:334-346.
Wilding et al. "Identification, Evolution, and Essentiality of the Mevalonate Pathway for Isopentenyl Diphosphate Biosynthesis in Gram-Positive Cocci" (2000) J Bacteriol 182(15):4319-4327.

* cited by examiner

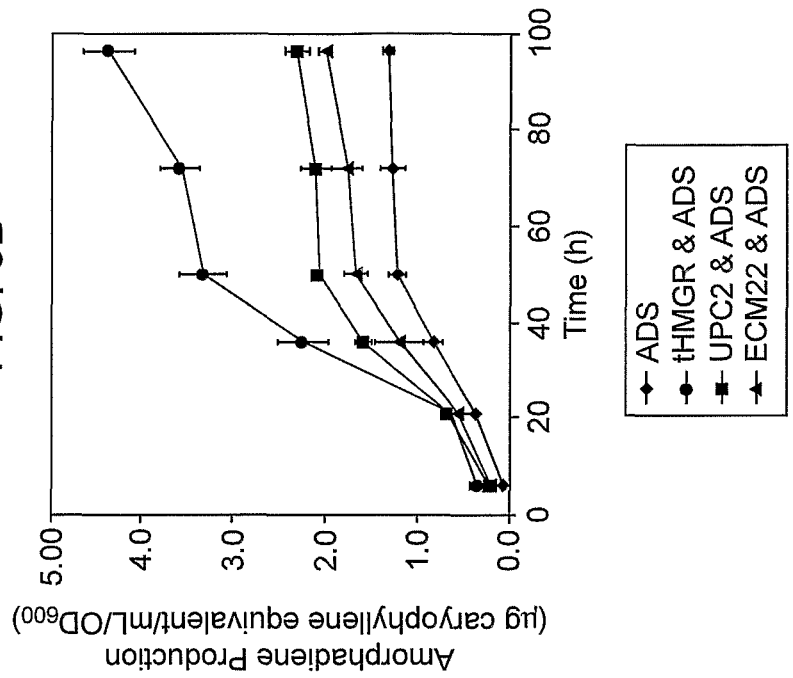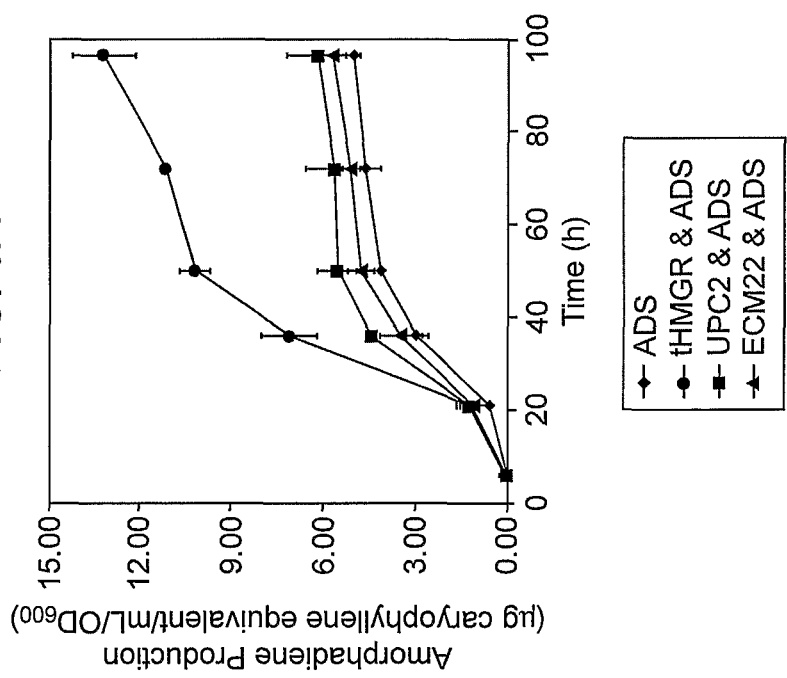

FIG. 6

Truncated HMGR coding sequence

ATGGTTTTAACCAATAAAACAGTCATTTCTGGATCGAAAGTCAAAAGTTTATCATCTGCGCAATCGAGCTC
ATCAGGACCTTCATCATCTAGTGAGGAAGATGATTCCCGCGATATTGAAAGCTTGGATAAGAAAATACGTC
CTTTAGAAGAATTAGAAGCATTATTAAGTAGTGGAAATACAAAACAATTGAAGAACAAAGAGGTCGCTGCC
TTGGTTATTCACGGTAAGTTACCTTTGTACGCTTTGGAGAAAAAATTAGGTGATACTACGAGAGCGGTTGC
GGTACGTAGGAAGGCTCTTTCAATTTTGGCAGAAGCTCCTGTATTAGCATCTGATCGTTTACCATATAAAA
ATTATGACTACGACCGCGTATTTGGCGCTTGTTGTGAAAATGTTATAGGTTACATGCCTTTGCCCGTTGGT
GTTATAGGCCCCTTGGTTATCGATGGTACATCTTATCATATACCAATGGCAACTACAGAGGGTTGTTTGGT
AGCTTCTGCCATGCGTGGCTGTAAGGCAATCAATGCTGGCGGTGGTGCAACAACTGTTTTAACTAAGGATG
GTATGACAAGAGGCCCAGTAGTCCGTTTCCCAACTTTGAAAAGATCTGGTGCCTGTAAGATATGGTTAGAC
TCAGAAGAGGGACAAAACGCAATTAAAAAAGCTTTTAACTCTACATCAAGATTTGCACGTCTGCAACATAT
TCAAACTTGTCTAGCAGGAGATTTACTCTTCATGAGATTTAGAACAACTACTGGTGACGCAATGGGTATGA
ATATGATTTCTAAAGGTGTCGAATACTCATTAAAGCAAATGGTAGAAGAGTATGGCTGGGAAGATATGGAG
GTTGTCTCCGTTTCTGGTAACTACTGTACCGACAAAAAACCAGCTGCCATCAACTGGATCGAAGGTCGTGG
TAAGAGTGTCGTCGCAGAAGCTACTATTCCTGGTGATGTTGTCAGAAAAGTGTTAAAAAGTGATGTTTCCG
CATTGGTTGAGTTGAACATTGCTAAGAATTTGGTTGGATCTGCAATGGCTGGGTCTGTTGGTGGATTTAAC
GCACATGCAGCTAATTTAGTGACAGCTGTTTTCTTGGCATTAGGACAAGATCCTGCACAAAATGTTGAAAG
TTCCAACTGTATAACATTGATGAAAGAAGTGGACGGTGATTTGAGAATTTCCGTATCCATGCCATCCATCG
AAGTAGGTACCATCGGTGGTGGTACTGTTCTAGAACCACAAGGTGCCATGTTGGACTTATTAGGTGTAAGA
GGCCCGCATGCTACCGCTCCTGGTACCAACGCACGTCAATTAGCAAGAATAGTTGCCTGTGCCGTCTTGGC
AGGTGAATTATCCTTATGTGCTGCCCTAGCAGCCGGCCATTTGGTTCAAAGTCATATGACCCACAACAGGA
AACCTGCTGAACCAACAAAACCTAACAATTTGGACGCCACTGATATAAATCGTTTGAAAGATGGGTCCGTC
ACCTGCATTAAATCCTAA (SEQ ID NO: 1)

FIG. 7A

```
Met Val Leu Thr Asn Lys Thr Val Ile Ser Gly Ser Lys Val Lys Ser
1               5                   10                  15
Leu Ser Ser Ala Gln Ser Ser Ser Gly Pro Ser Ser Ser Ser Ser Glu
            20                  25                  30
Glu Asp Asp Ser Arg Asp Ile Glu Ser Leu Asp Lys Lys Ile Arg Pro
        35                  40                  45
Leu Glu Glu Leu Glu Ala Leu Leu Ser Ser Gly Asn Thr Lys Gln Leu
    50                  55                  60
Lys Asn Lys Glu Val Ala Ala Leu Val Ile His Gly Lys Leu Pro Leu
65                  70                  75                  80
Tyr Ala Leu Glu Lys Lys Leu Gly Asp Thr Thr Arg Ala Val Ala Val
            85                  90                  95
Arg Arg Lys Ala Leu Ser Ile Leu Ala Glu Ala Pro Val Leu Ala Ser
            100                 105                 110
Asp Arg Leu Pro Tyr Lys Asn Tyr Asp Tyr Asp Arg Val Phe Gly Ala
        115                 120                 125
Cys Cys Glu Asn Val Ile Gly Tyr Met Pro Leu Pro Val Gly Val Ile
    130                 135                 140
Gly Pro Leu Val Ile Asp Gly Thr Ser Tyr His Ile Pro Met Ala Thr
145                 150                 155                 160
Thr Glu Gly Cys Leu Val Ala Ser Ala Met Arg Gly Cys Lys Ala Ile
            165                 170                 175
Asn Ala Gly Gly Gly Ala Thr Thr Val Leu Thr Lys Asp Gly Met Thr
            180                 185                 190
Arg Gly Pro Val Val Arg Phe Pro Thr Leu Lys Arg Ser Gly Ala Cys
        195                 200                 205
Lys Ile Trp Leu Asp Ser Glu Glu Gly Gln Asn Ala Ile Lys Lys Ala
    210                 215                 220
Phe Asn Ser Thr Ser Arg Phe Ala Arg Leu Gln His Ile Gln Thr Cys
225                 230                 235                 240
Leu Ala Gly Asp Leu Leu Phe Met Arg Phe Arg Thr Thr Thr Gly Asp
            245                 250                 255
Ala Met Gly Met Asn Met Ile Ser Lys Gly Val Glu Tyr Ser Leu Lys
            260                 265                 270
Gln Met Val Glu Glu Tyr Gly Trp Glu Asp Met Glu Val Val Ser Val
        275                 280                 285
Ser Gly Asn Tyr Cys Thr Asp Lys Lys Pro Ala Ala Ile Asn Trp Ile
    290                 295                 300
Glu Gly Arg Gly Lys Ser Val Val Ala Glu Ala Thr Ile Pro Gly Asp
305                 310                 315                 320
Val Val Arg Lys Val Leu Lys Ser Asp Val Ser Ala Leu Val Glu Leu
            325                 330                 335
Asn Ile Ala Lys Asn Leu Val Gly Ser Ala Met Ala Gly Ser Val Gly
            340                 345                 350
Gly Phe Asn Ala His Ala Ala Asn Leu Val Thr Ala Val Phe Leu Ala
        355                 360                 365
Leu Gly Gln Asp Pro Ala Gln Asn Val Glu Ser Ser Asn Cys Ile Thr
    370                 375                 380
Leu Met Lys Glu Val Asp Gly Asp Leu Arg Ile Ser Val Ser Met Pro
385                 390                 395                 400
```

FIG. 7B

```
Ser Ile Glu Val Gly Thr Ile Gly Gly Gly Thr Val Leu Glu Pro Gln
            405                 410                 415
Gly Ala Met Leu Asp Leu Leu Gly Val Arg Gly Pro His Ala Thr Ala
            420                 425                 430
Pro Gly Thr Asn Ala Arg Gln Leu Ala Arg Ile Val Ala Cys Ala Val
            435                 440                 445
Leu Ala Gly Glu Leu Ser Leu Cys Ala Ala Leu Ala Ala Gly His Leu
    450                 455                 460
Val Gln Ser His Met Thr His Asn Arg Lys Pro Ala Glu Pro Thr Lys
465                 470                 475                 480
Pro Asn Asn Leu Asp Ala Thr Asp Ile Asn Arg Leu Lys Asp Gly Ser
            485                 490                 495
Val Thr Cys Ile Lys Ser (SEQ ID NO: 2)
            500
```

GENETICALLY MODIFIED HOST CELLS AND USE OF SAME FOR PRODUCING ISOPRENOID COMPOUNDS

CROSS-REFERENCE

This application is a continuation of U.S. patent application Ser. No. 14/451,056, filed Aug. 4, 2014, now U.S. Pat. No. 9,809,829, which is a continuation of U.S. patent application Ser. No. 11/571,315, filed Nov. 13, 2007, now U.S. Pat. No. 8,828,684, which is a national stage application under 35 U.S.C. § 371 of PCT/US2005/026190, filed Jul. 21, 2005, which claims the benefit of U.S. Provisional Patent Application No. 60/592,009 filed Jul. 27, 2004, each of which application is incorporated herein by reference in its entirety.

FIELD OF THE INVENTION

The present invention is in the field of production of isoprenoid compounds, and in particular host cells that are genetically modified to produce isoprenoid compounds.

BACKGROUND OF THE INVENTION

Isoprenoids constitute an extremely large and diverse group of natural products that have a common biosynthetic origin, i.e., a single metabolic precursor, isopentenyl diphosphate (IPP). Isoprenoid compounds are also referred to as "terpenes" or "terpenoids." Over 40,000 isoprenoids have been described. By definition, isoprenoids are made up of so-called isoprene (C5) units. The number of C-atoms present in the isoprenoids is typically divisible by five (C5, C10, C15, C20, C25, C30 and C40), although irregular isoprenoids and polyterpenes have been reported. Important members of the isoprenoids include the carotenoids, sesquiterpenoids, diterpenoids, and hemiterpenes. Carotenoids include, e.g., lycopene, β-carotene, and the like, many of which function as antioxidants. Sesquiterpenoids include, e.g., artemisinin, a compound having anti-malarial activity. Diterpenoids include, e.g., taxol, a cancer chemotherapeutic agent.

Isoprenoids comprise the most numerous and structurally diverse family of natural products. In this family, terpenoids isolated from plants and other natural sources are used as commercial flavor and fragrance compounds as well as antimalarial and anticancer drugs. A majority of the terpenoid compounds in use today are natural products or their derivatives. The source organisms (e.g., trees, marine invertebrates) of many of these natural products are neither amenable to the large-scale cultivation necessary to produce commercially viable quantities nor to genetic manipulation for increased production or derivatization of these compounds. Therefore, the natural products must be produced semi-synthetically from analogs or synthetically using conventional chemical syntheses. Furthermore, many natural products have complex structures, and, as a result, are currently uneconomical or impossible to synthesize. Such natural products must be either extracted from their native sources, such as trees, sponges, corals and marine microbes; or produced synthetically or semi-synthetically from more abundant precursors. Extraction of a natural product from a native source is limited by the availability of the native source; and synthetic or semi-synthetic production of natural products can suffer from low yield and/or high cost. Such production problems and limited availability of the natural source can restrict the commercial and clinical development of such products.

The biosynthesis of isoprenoid natural products in engineered host cells could tap the unrealized commercial and therapeutic potential of these natural resources and yield less expensive and more widely available fine chemicals and pharmaceuticals. A major obstacle to high level terpenoid biosynthesis is the production of terpene precursors. In *Saccharomyces cerevisiae*, the mevalonate pathway provides for production of isopentenyl diphosphate (IPP), which can be isomerized and polymerized into isoprenoids and terpenes of commercial value. Other valuable precursors are also produced, including farnesyl diphosphate (FPP) and geranylgeranyl diphosphate (GPP). However, much of the reaction flux is directed towards the undesired later steps of the sterol pathway, resulting in the production of ergosterol.

There is a need in the art for improved isoprenoid-producing or isoprenoid precursor-producing host cells that provide for high-level production of isoprenoid compounds, as well as the polyprenyl diphosphate precursors of such compounds. The present invention addresses this need and provides related advantages.

Literature

U.S. Patent Publication No. 2004/005678; U.S. Patent Publication No. 2003/0148479;

Martin et al. (2003) Nat. Biotech. 21(7):796-802; Polakowski et al. (1998) Appl. Biotechnol. 49: 67-71; Wilding et al. (2000) J Bacteriol 182(15): 4319-27; U.S. Patent Publication No. 2004/0194162; Donald et al. (1997) Appl. Env. Microbiol. 63:3341-3344; Jackson et al. (2003) Organ. Lett. 5:1629-1632; U.S. Patent Publication No. 2004/0072323; U.S. Patent Publication No. 2004/0029239; U.S. Patent Publication No. 2004/0110259; U.S. Patent Publication No. 2004/0063182; U.S. Pat. No. 5,460,949; U.S. Patent Publication No. 2004/0077039; U.S. Pat. Nos. 6,531,303; 6,689,593; Hamano et al. (2001) Biosci. Biotechnol. Biochem. 65:1627-1635; T. Kuzuyama. (2004) Biosci. Biotechnol. Biochem. 68(4): 931-934; T. Kazuhiko. (2004) Biotechnology Letters. 26: 1487-1491; Brock et al. (2004) Eur J. Biochem. 271: 3227-3241; Choi, et al. (1999) Appl. Environ. Microbio. 65 4363-4368; Parke et al., (2004) Appl. Environ. Microbio. 70: 2974-2983; Subrahmanyam et al. (1998) J. Bact. 180: 4596-4602; Murli et al. (2003) J. Ind. Microbiol. Biotechnol. 30: 500-509.

SUMMARY OF THE INVENTION

The present invention provides genetically modified eukaryotic host cells that produce isoprenoid precursors or isoprenoid compounds. A subject genetically modified host cell comprises increased activity levels of one or more of mevalonate pathway enzymes, increased levels of prenyl transferase activity, and decreased levels of squalene synthase activity. Methods are provided for the production of an isoprenoid compound or an isoprenoid precursor in a subject genetically modified eukaryotic host cell. The methods generally involve culturing a subject genetically modified host cell under conditions that promote production of high levels of an isoprenoid or isoprenoid precursor compound.

BRIEF DESCRIPTION OF THE DRAWINGS

FIGS. 3A and 3B depict production of amorphadiene by S. cerevisiae over 96 hours of culture expressing amorphadiene synthase (ADS) (♦); ADS and truncated 3-hydroxy-3-methylglutaryl coenzyme-A reductase (tHMGR) (●); ADS and upc2-1 (■); and ADS and ecm22-1 (▲). The data are shown as total production (3A) and normalized for cell density (3B). The data are means ±standard deviations (n=3).

FIG. 6 depicts a nucleotide sequence encoding a truncated HMGR.

FIGS. 7A and 7B depict an amino acid sequence of a truncated HMGR.

DEFINITIONS

Figure 1:
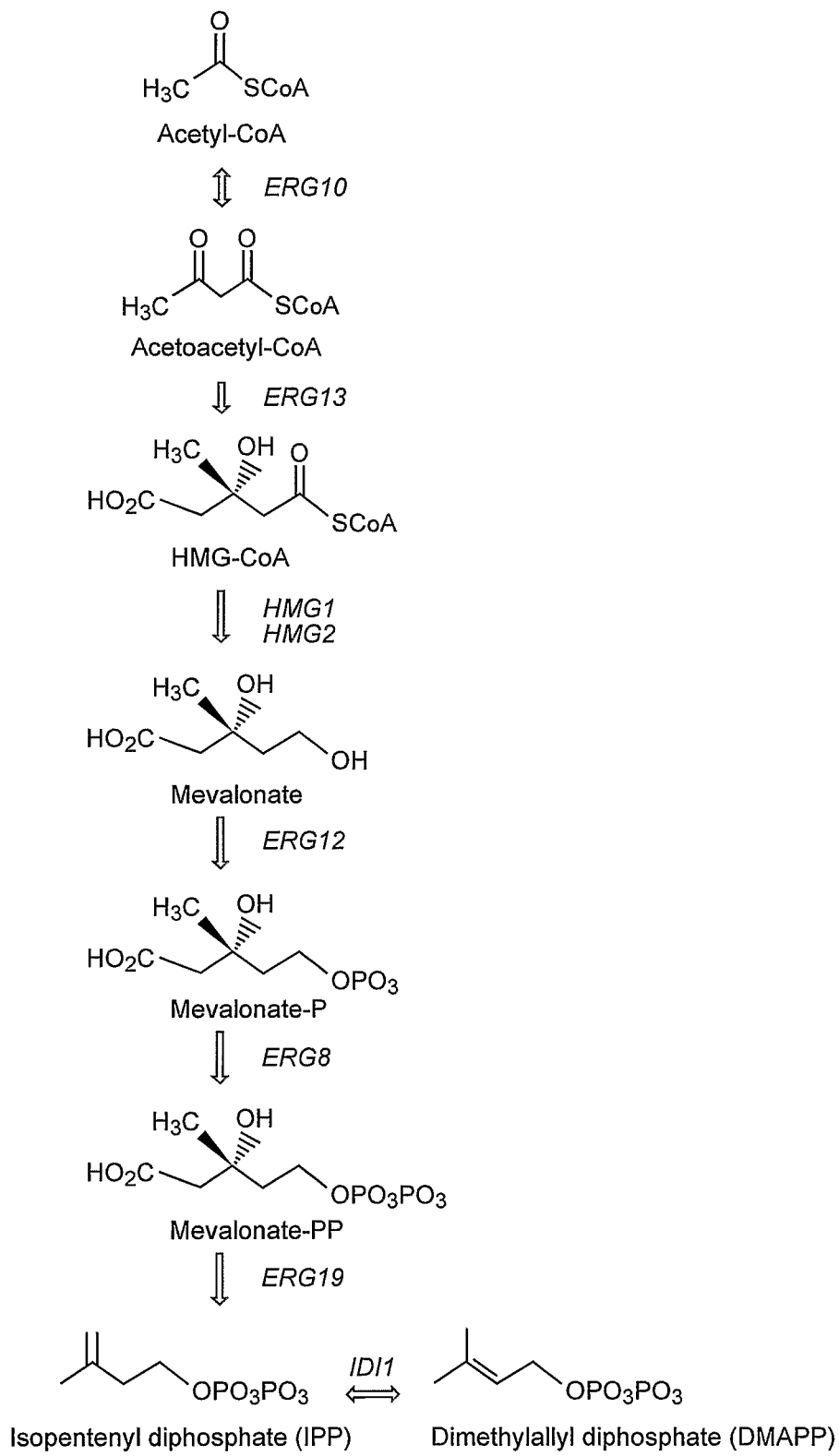
FIG. 1 is a schematic representation of the mevalonate pathway in Saccharomyces cerevisiae. The structures of intermediates and gene names encoding the various enzymes in the pathway are shown.

The terms "isoprenoid," "isoprenoid compound," "terpene," "terpene compound," "terpenoid," and "terpenoid compound" are used interchangeably herein. Isoprenoid compounds are made up various numbers of so-called isoprene (C5) units. The number of C-atoms present in the isoprenoids is typically evenly divisible by five (e.g., C5, C10, C15, C20, C25, C30 and C40). Irregular isoprenoids and polyterpenes have been reported, and are also included in the definition of "isoprenoid." Isoprenoid compounds include, but are not limited to, monoterpenes, sesquiterpenes, triterpenes, polyterpenes, and diterpenes.

As used herein, the term "prenyl diphosphate" is used interchangeably with "prenyl pyrophosphate," and includes monoprenyl diphosphates having a single prenyl group (e.g., IPP and DMAPP), as well as polyprenyl diphosphates that include 2 or more prenyl groups. Monoprenyl diphosphates include isopentenyl pyrophosphate (IPP) and its isomer dimethylallyl pyrophosphate (DMAPP).

As used herein, the term "terpene synthase" refers to any enzyme that enzymatically modifies IPP, DMAPP, or a polyprenyl pyrophosphate, such that a terpenoid compound is produced. The term "terpene synthase" includes enzymes that catalyze the conversion of a prenyl diphosphate into an isoprenoid.

The word "pyrophosphate" is used interchangeably herein with "diphosphate." Thus, e.g., the terms "prenyl diphosphate" and "prenyl pyrophosphate" are interchangeable; the terms "isopentenyl pyrophosphate" and "isopentenyl diphosphate" are interchangeable; the terms farnesyl diphosphate" and "farnesyl pyrophosphate" are interchangeable; etc.

The term "mevalonate pathway" or "MEV pathway" is used herein to refer to the biosynthetic pathway that converts acetyl-CoA to IPP. The mevalonate pathway comprises enzymes that catalyze the following steps: (a) condensing two molecules of acetyl-CoA to acetoacetyl-CoA; (b) condensing acetoacetyl-CoA with acetyl-CoA to form HMG-CoA; (c) converting HMG-CoA to mevalonate; (d) phosphorylating mevalonate to mevalonate 5-phosphate; (e) converting mevalonate 5-phosphate to mevalonate 5-pyrophosphate; and (f) converting mevalonate 5-pyrophosphate to isopentenyl pyrophosphate. The mevalonate pathway is illustrated schematically in FIG. 1.

As used herein, the term "prenyl transferase" is used interchangeably with the terms "isoprenyl diphosphate synthase" and "polyprenyl synthase" (e.g., "GPP synthase," "FPP synthase," "OPP synthase," etc.) to refer to an enzyme that catalyzes the consecutive 1'-4 condensation of isopentenyl diphosphate with allylic primer substrates, resulting in the formation of prenyl diphosphates of various chain lengths.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

As used herein, the terms "operon" and "single transcription unit" are used interchangeably to refer to two or more contiguous coding regions (nucleotide sequences that encode a gene product such as an RNA or a protein) that are coordinately regulated by one or more controlling elements (e.g., a promoter). As used herein, the term "gene product" refers to RNA encoded by DNA (or vice versa) or protein that is encoded by an RNA or DNA, where a gene will typically comprise one or more nucleotide sequences that encode a protein, and may also include introns and other non-coding nucleotide sequences.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The term "naturally-occurring" as used herein as applied to a nucleic acid, a cell, or an organism, refers to a nucleic acid, cell, or organism that is found in nature. For example, a polypeptide or polynucleotide sequence that is present in an organism (including viruses) that can be isolated from a source in nature and which has not been intentionally modified by a human in the laboratory is naturally occurring.

The term "heterologous nucleic acid," as used herein, refers to a nucleic acid wherein at least one of the following is true: (a) the nucleic acid is foreign ("exogenous") to (i.e., not naturally found in) a given host microorganism or host cell; (b) the nucleic acid comprises a nucleotide sequence that is naturally found in (e.g., is "endogenous to") a given host microorganism or host cell (e.g., the nucleic acid comprises a nucleotide sequence endogenous to the host microorganism or host cell); however, in the context of a heterologous nucleic acid, the same nucleotide sequence as found endogenously is produced in an unnatural (e.g., greater than expected or greater than naturally found) amount in the cell, or a nucleic acid comprising a nucleotide sequence that differs in. sequence from the endogenous nucleotide sequence but encodes the same protein (having the same or substantially the same amino acid sequence) as found endogenously is produced in an unnatural (e.g., greater than expected or greater than naturally found) amount in the cell; (c) the nucleic acid comprises two or more nucleotide sequences that are not found in the same relationship to each other in nature, e.g., the nucleic acid is recombinant. An example of a heterologous nucleic acid is a nucleotide sequence encoding HMGR operably linked to a transcriptional control element (e.g., a promoter) to which an endogenous (naturally-occurring) HMGR coding sequence is not normally operably linked. Another example of a heterologous nucleic acid a high copy number plasmid comprising a nucleotide sequence encoding HMGR. Another example of a heterologous nucleic acid is a nucleic acid encoding HMGR, where a host cell that does not normally produce HMGR is genetically modified with the nucleic acid encoding HMGR; because HMGR-encoding nucleic acids are not naturally found in the host cell, the nucleic acid is heterologous to the genetically modified host cell.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is perfoimed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

By "construct" is meant a recombinant nucleic acid, generally recombinant DNA, which has been generated for the purpose of the expression of a specific nucleotide sequence(s), or is to be used in the construction of other recombinant nucleotide sequences.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell. For example, a cDNA generated from mRNA isolated from a plant and encoding a terpene synthase represents an exogenous nucleic acid to S. cerevisiae. In S. cerevisiae, nucleotide sequences encoding HMGS, MK, and PMK on the chromosome would be "endogenous" nucleic acids.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (i.e., DNA exogenous to the cell). Genetic change ("modification") can be accomplished either by incorporation of the new DNA into the genome of the host cell, or by transient or stable maintenance of the new DNA as an episomal element. Where the cell is a eukaryotic cell, a permanent genetic change is generally achieved by introduction of the DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell or a cell from a multicellular organism (e.g., a cell line) cultured as a unicellular entity, which eukaryotic cells can be, or have been, used as recipients for a nucleic acid (e.g., an expression vector that comprises a nucleotide sequence encoding one or more gene products such as mevalonate pathway gene products), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject eukaryotic host cell is a genetically modified eukaryotic host cell, by virtue of introduction into a suitable eukaryotic host cell a heterologous nucleic acid, e.g., an exogenous nucleic acid that is foreign to the eukaryotic host cell, or a recombinant nucleic acid that is not normally found in the eukaryotic host cell.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

Expression cassettes may be prepared comprising a transcription initiation or transcriptional control region(s) (e.g., a promoter), the coding region for the protein of interest, and a transcriptional termination region. Transcriptional control regions include those that provide for over-expression of the protein of interest in the genetically modified host cell; those that provide for inducible expression, such that when an inducing agent is added to the culture medium, transcription of the coding region of the protein of interest is induced or increased to a higher level than prior to induction.

A nucleic acid is "hybridizable" to another nucleic acid, such as a cDNA, genomic DNA, or RNA, when a single stranded form of the nucleic acid can anneal to the other nucleic acid under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Hybridization conditions and post-hybridization washes are useful to obtain the desired determine stringency conditions of the hybridization. One set of illustrative post-hybridization washes is a series of washes starting with 6×SSC (where SSC is 0.15 M NaCl and 15 mM citrate buffer), 0.5% SDS at room temperature for 15 minutes, then repeated with 2 ×SSC, 0.5% SDS at 45° C. for 30 minutes, and then repeated twice with 0.2×SSC, 0.5% SDS at 50° C. for 30 minutes. Other stringent conditions are obtained by using higher temperatures in which the washes are identical to those above except for the temperature of the final two 30 minute washes in 0.2×SSC, 0.5% SDS, which is increased to 60° C. Another set of highly stringent conditions uses two final washes in 0.1×SSC, 0.1% SDS at 65° C. Another example of stringent hybridization conditions is hybridization at 50° C. or higher and 0.1x SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C. Stringent hybridization conditions and post-hybridization wash conditions are hybridization conditions and post-hybridization wash conditions that are at least as stringent as the above representative conditions.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of the melting temperature (Tm) for hybrids of nucleic acids having those sequences. The relative stability (corresponding to higher Tm) of nucleic acid hybridizations decreases in the following order: RNA:RNA, DNA:RNA, DNA:DNA.

For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; and at least about 30 nucleotides. Furthermore, the skilled artisan will recognize that the temperature and wash solution salt concentration may be adjusted as necessary according to factors such as length of the probe.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acids substitution groups are: valine-leucine-isoleucine, phenylalanine-tyrosine, lysine-arginine, alanine-valine, and asparagine-glutamine.

"Synthetic nucleic acids" can be assembled from oligonucleotide building blocks that are chemically synthesized using procedures known to those skilled in the art. These building blocks are ligated and annealed to form gene segments which are then enzymatically assembled to construct the entire gene. "Chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. The nucleotide sequence of the nucleic acids can be modified for optimal expression based on optimization of nucleotide sequence to reflect the codon bias of the host cell. The skilled artisan appreciates the likelihood of successful expression if codon usage is biased towards those codons favored by the host. Determination of preferred codons can be based on a survey of genes derived from the host cell where sequence information is available.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), J. Mol. Biol. 215:403-10. Another alignment algorithm is FASTA, available in the Genetics Computing Group (GCG) package, from Madison, Wisconsin, USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, California, USA. Of particular interest are alignment programs that permit gaps in the sequence. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. See J. Mol. Biol. 48: 443-453 (1970).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a genetically modified host cell" includes a plurality of such genetically modified host cells and reference to "the isoprenoid compound" includes reference to one or more isoprenoid compounds and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides genetically modified eukaryotic host cells that produce isoprenoid precursors or isoprenoid compounds. A subject genetically modified host cell comprises increased activity levels of one or more of mevalonate pathway enzymes, increased levels of prenyl transferase activity, and decreased levels of squalene synthase activity. Methods are provided for the production of an isoprenoid compound or an isoprenoid precursor in a subject genetically modified eukaryotic host cell. The methods generally involve culturing a subject genetically modified host cell under conditions that promote production of high levels of an isoprenoid or isoprenoid precursor compound.

Figure 2:
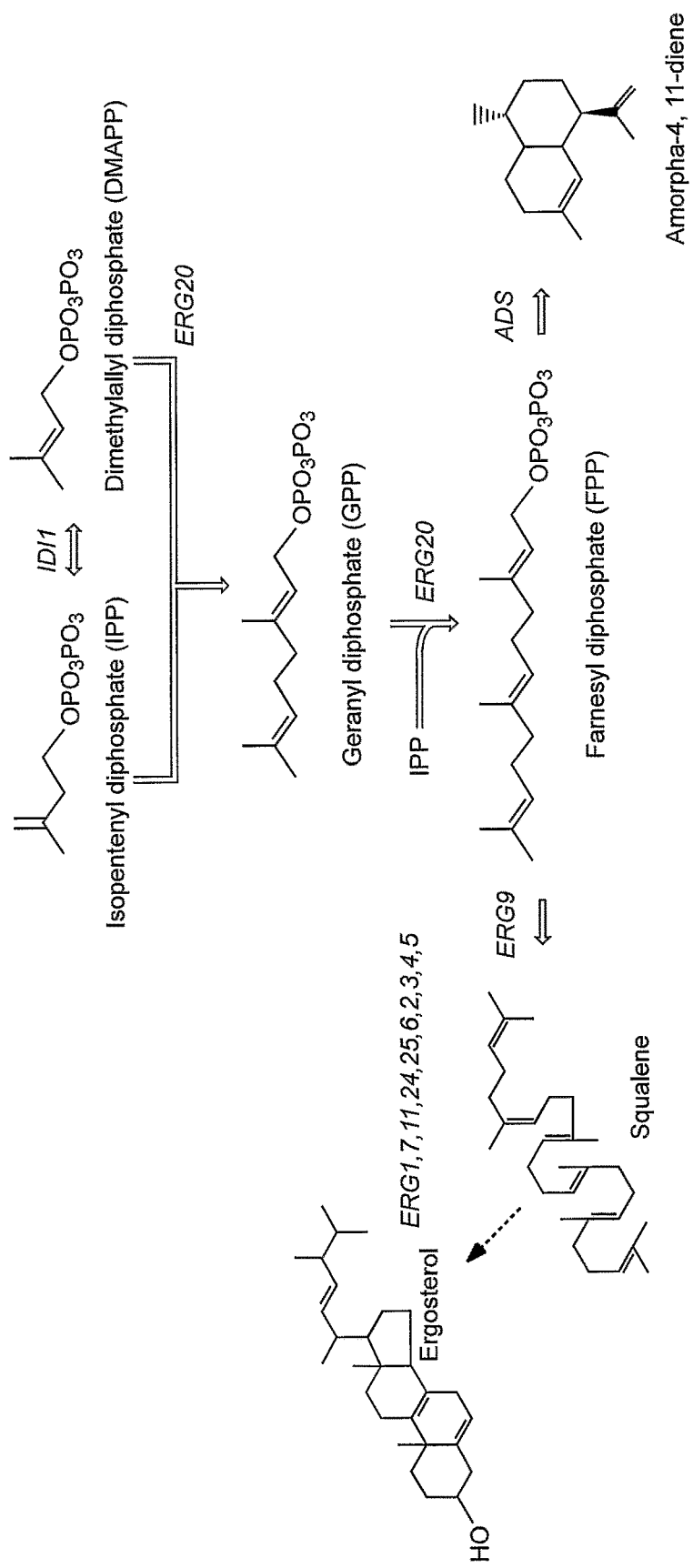
FIG. 2 is a schematic representation of a portion of the sterol biosynthesis pathway in an organism expressing amorphadiene synthase (ADS). The structures of intermediates and the names of genes encoding the various enzymes in the pathway are shown.

The *S. cerevisiae* mevalonate and sterol pathways are depicted schematically in FIG. 1 and FIG. 2 (note that amorphadiene synthase (ADS) in FIG. 2 is not normally expressed in genetically unmodified *S. cerevisiae*.) This pathway is typical of a wide variety of eukaryotic cells. FPP is converted to squalene by squalene synthase (ERG9). Squalene is converted to ergosterol in subsequent steps. In unmodified cells, much of the metabolic flux directs FPP towards sterol synthesis. In a subject genetically modified eukaryotic host cell, the metabolic flux is redirected towards greater production of the isoprenoid precursors IPP and FPP.

Genetically Modified Host Cells

The present invention provides genetically modified eukaryotic host cells, which cells comprise one or more genetic modifications that provide for increased production of isoprenoid or isoprenoid precursor compounds. Compared to a control host cell not genetically modified according to the present invention, a subject genetically modified host cell exhibits the following characteristics: increased activity levels of one or more mevalonate pathway enzymes; increased levels of prenyl transferase activity; and decreased levels of squalene synthase activity.

Increased activity levels of one or more mevalonate pathway enzymes, increased levels of prenyl transferase activity, and decreased levels of squalene synthase activity increases isoprenoid or isoprenoid precursor production by a subject genetically modified host cell. Thus, in some embodiments, a subject genetically modified host cell exhibits increases in isoprenoid or isoprenoid precursor production, where isoprenoid or isoprenoid precursor production is increased by at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about $10^3$-fold, or more, in the genetically modified host cell, compared to the level of isoprenoid precursor or isoprenoid compound produced in a control host cell that is not genetically modified as described herein. Isoprenoid or isoprenoid precursor production is readily determined using well-known methods, e.g., gas chromatography-mass spectrometry, liquid chromatography-mass spectrometry, ion chromatography-mass spectrometry, pulsed amperometric detection, uv-vis spectrometry, and the like.

In some embodiments, a subject genetically modified host cell provides for enhanced production of isoprenoid or isoprenoid precursor per cell, e.g., the amount of isoprenoid or isoprenoid precursor compound produced using a subject method is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or $10^3$-fold, or more, higher than the amount of the isoprenoid or isoprenoid precursor compound produced by a host cell that is not genetically modified by the subject methods, on a per cell basis. Amount of cells is measured by measuring dry cell weight or measuring optical density of the cell culture.

In other embodiments, a subject genetically modified host cell provides for enhanced production of isoprenoid or isoprenoid precursor per unit volume of cell culture, e.g., the amount of isoprenoid or isoprenoid precursor compound produced using a subject genetically modified host cell is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or $10^3$-fold, or more, higher than the amount of the isoprenoid or isoprenoid precursor compound produced by a host cell that is not genetically modified by the subject methods, on a per unit volume of cell culture basis.

In some embodiments, a subject genetically modified eukaryotic host produces an isoprenoid or isoprenoid precursor compound in an amount ranging from 1µg isoprenoid compound/ml to 100,000 µg isoprenoid compound/ml, e.g., from about 1 µg/ml to about 10,000 µg/ml of isoprenoid compound, 1 µg/ml to 5000 µg/ml of isoprenoid compound, 1 µg/ml to 4500 µg/ml of isoprenoid compound, 1 µg/ml to 4000 µg/ml of isoprenoid compound, 1 g/ml to 3500 µg/ml of isoprenoid compound, 1 µg/ml to 3000 µg/ml of isoprenoid compound, 1 µg/ml to 2500 µg/ml of isoprenoid compound, 1µg/ml to 2000 µg/ml of isoprenoid compound, 1 µg/ml to 1500 µg/ml of isoprenoid compound, 1 µg/ml to 1000 µg/ml of isoprenoid compound, 5µg/ml to 5000µg/ml of isoprenoid compound, 10 µg/ml to 5000 µg/ml of isoprenoid compound, 20 µg/ml to 5000 µg/ml of isoprenoid compound, 30 µg/ml to 1000 µg/ml of isoprenoid compound, 40 µg/ml to 500 µg/ml of isoprenoid compound, 50 µg/ml to 300 µg/ml of isoprenoid compound, 60 µg/ml to 100 µg/ml of isoprenoid compound, 70 µg/ml to 80 µg/ml of isoprenoid compound, from about 1 µg/ml to about 1,000 µg/ml, from about 1,000 µg/ml to about 2,000 µg/ml, from about 2,000 µg/ml to about 3,000 µg/ml, from about 3,000 µg/ml to about 4,000 µg/ml, from about 4,000 µg/ml to about 5,000 µg/ml, from about 5,000 µg/ml to about 7,500 µg/ml, or from about 7,500 µg/ml to about 10,000 µg/ml, or greater than 10,000 µg/ml isoprenoid compound, e.g., from about 10 mg isoprenoid compound/ml to about 20 mg isoprenoid compound/ml, from about 20 mg isoprenoid compound/ml to about 50 mg isoprenoid compound/ml, from about 50 mg isoprenoid compound/ml to about 100 mg isoprenoid compound/ml, or more.

The subject methods can be used in a variety of different kinds of eukaryotic host cells. Host cells are, in many embodiments, unicellular organisms, or are grown in culture as single cells. Suitable eukaryotic host cells include, but are not limited to, yeast cells, insect cells, plant cells, fungal cells, and algal cells. Suitable eukaryotic host cells include, but are not limited to, *Pichia pastoris*, *Pichia finlandica*, *Pichia trehalophila*, *Pichia koclamae*, *Pichia membranaefaciens*, *Pichia opuntiae*, *Pichia thermotolerans*, *Pichia salictaria*, *Pichia guercuum*, *Pichia pijperi*, *Pichia stiptis*, *Pichia methanolica*, *Pichia*sp., *Saccharomyces cerevisiae*, *Saccharomyces* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, *Neurospora crassa*, *Chlamydomonas reinhardtii*, and the like. In some embodiments, the host cell is a eukaryotic cell other than a plant cell. In some embodiments, subject genetically modified host cell is a yeast cell. In a particular embodiment, the yeast cell is *Saccharomyces cerevisiae*.

In an exemplary embodiment, the metabolic pathway of *Saccharomyces cerevisiae* is engineered to produce sesquiterpenes from farnesyl diphosphate. One such sesquiterpene, amorphadiene, is a precursor to the antimalarial drug artemisinin. Amorphadiene, cyclized from farnesyl diphosphate, can be used as an assay for isoprenoid precursor levels.

In an exemplary embodiment, activity levels of HMGR, a prenyl transferase, Ecm22p and Upc2p are increased and activity levels of squalene synthase are decreased. 3-hydroxy-3-methylglutaryl coenzyme-A reductase (HMGR) and a prenyl transferase, e.g., farnesyl diphosphate synthase (FPPS), catalyze bottle neck reactions in an amorphadiene synthesis pathway. Increasing activity of HMGR and a prenyl transferase, e.g., FPPS, overcomes these bottlenecks. Two transcription factors, Ecm22p and Upc2p, are important in sterol synthesis regulation. Each of these two factors is mutated at a single amino acid near their C-termini, which mutation increases activity of each factor. Squalene synthase catalyzes the reaction from farnesyl diphosphate to squalene in the undesired sterol synthesis pathway. Thus, to maximize precursor pools and prevent undue flux to sterols, transcription of ERG9 has been limited.

Increased Level of Activity of One or More Mevalonate Pathway Enzymes

The mevalonate pathway comprises enzymes that catalyze the following steps: (a) condensing two molecules of acetyl-CoA to acetoacetyl-CoA, typically by action of acetoacetyl-CoA thiolase; (b) condensing acetoacetyl-CoA with acetyl-CoA to form HMG-CoA, typically by action of HMG synthase (HMGS); (c) converting HMG-CoA to mevalonate, typically by action of HMGR; (d) phosphorylating mevalonate to mevalonate 5-phosphate, typically by action of mevalonate kinase (MK); (e) converting mevalonate 5-phosphate to mevalonate 5-pyrophosphate, typically by action of phosphomevalonate kinase (PMK); and (f) converting mevalonate 5-pyrophosphate to isopentenyl pyrophosphate, typically by action of mevalonate pyrophosphate decarboxylase (MPD).

A subject genetically modified eukaryotic host cell comprises one or more genetic modifications resulting in one or more of the following: increased level of HMGS activity; increased level of HMGR activity; increased level of MK activity; increased level of PMK activity; and increased level of MPD activity.

In some embodiments, a subject genetically modified host cell is genetically modified such that the level of activity of one or more mevalonate pathway enzymes is increased. The level of activity of one or more mevalonate pathway enzymes in a subject genetically modified host cell can be increased in a number of ways, including, but not limited to, 1) increasing the promoter strength of the promoter to which the mevalonate pathway enzyme coding region is operably linked; 2) increasing the copy number of the plasmid comprising a nucleotide sequence encoding the mevalonate pathway enzyme; 3) increasing the stability of a mevalonate pathway enzyme mRNA (where a "mevalonate pathway enzyme mRNA" is an mRNA comprising a nucleotide sequence encoding the mevalonate pathway enzyme); 4) modifying the sequence of the ribosome binding site of a mevalonate pathway enzyme mRNA such that the level of translation of the mevalonate pathway enzyme mRNA is increased; 5) modifying the sequence between the ribosome binding site of a mevalonate pathway enzyme mRNA and the start codon of the mevalonate pathway enzyme coding sequence such that the level of translation of the mevalonate pathway enzyme mRNA is increased; 6) modifying the entire intercistronic region 5' of the start codon of the mevalonate pathway enzyme coding region such that translation of the mevalonate pathway enzyme mRNA is increased; 7) modifying the codon usage of mevalonate pathway enzyme such that the level of translation of the mevalonate pathway enzyme mRNA is increased, 8) expressing rare codon tRNAs used in the mevalonate pathway enzyme such that the level of translation of the mevalonate pathway enzyme mRNA is increased; 9) increasing the enzyme stability of mevalonate pathway enzyme; 10) increasing the specific activity (units activity per unit protein) of the mevalonate pathway enzyme; 11) expressing a modified form of a mevalonate pathway enzyme such that the modified enzyme exhibits increased solubility in the host cell; or 12) expressing a modified form of a mevalonate pathway enzyme such that the modified enzyme lacks a domain through which regulation occurs. The foregoing modifications may be made singly or in combination; e.g., two or more of the foregoing modifications may be made to provide for an increased level of mevalonate pathway enzyme activity.

The enzyme HMG-CoA reductase (HMGR) catalyzes an irreversible reaction that reduces 3-hydroxy-3-methylglutaryl Coenzyme A (HMG-CoA) to mevalonate. This step is the committed step in the sterol biosynthesis pathway. Thus, HMGR is a major point of regulation in organisms that naturally utilize the mevalonate pathway to produce isoprenoids.

In some embodiments, a subject genetically modified host cell is genetically modified such that the level of HMGR activity is increased. The level of HMGR activity in the genetically modified host cell can be increased in a number of ways, including, but not limited to, 1) increasing the promoter strength of the promoter to which the HMGR coding region is operably linked; 2) increasing the copy number of the plasmid comprising a nucleotide sequence encoding HMGR; 3) increasing the stability of an HMGR mRNA (where an "HMGR mRNA" is an mRNA comprising a nucleotide sequence encoding HMGR); 4) modifying the sequence of the ribosome binding site of an HMGR mRNA such that the level of translation of the HMGR mRNA is increased; 5) modifying the sequence between the ribosome binding site of an HMGR mRNA and the start codon of the HMGR coding sequence such that the level of translation of the HMGR mRNA is increased; 6) modifying the entire intercistronic region 5' of the start codon of the HMGR coding region such that translation of the HMGR mRNA is increased; 7) modifying the codon usage of HMGR such that the level of translation of the HMGR mRNA is increased, 8) expressing rare codon tRNAs used in HMGR such that the level of translation of the HMGR mRNA is increased; 9) increasing the enzyme stability of HMGR; 10) increasing the specific activity (units activity per unit protein) of HMGR; or 11) truncating the HMGR to remove a negative regulatory element. The foregoing modifications may be made singly or in combination; e.g., two or more of the foregoing modifications may be made to provide for an increased level of HMGR activity.

In many embodiments, the level of HMGR is increased by genetically modifying a eukaryotic host cell such that it produces a truncated form of HMGR (tHMGR), which truncated form has increased enzymatic activity relative to wild-type HMGR. tHMGR lacks a membrane-spanning domain and is therefore soluble and lacks the feedback inhibition of HMGR. tHMGR retains its catalytic C-terminus region, and thus retains the activity of HMGR. In some embodiments, the truncated HMGR has the amino acid sequence depicted in FIGS. 7A and 7B (SEQ ID NO:2). In some embodiments, the truncated HMGR is encoded by a nucleic acid comprising the nucleotide sequence depicted in FIG. 6 (SEQ ID NO:1).

In some embodiments, the level of activity of one or more of HMGS, MK, and PMK is increased. In *S. cerevisiae*, the genes encoding HMGS (ERG13), MK (ERG12), and PMK (ERG8) comprise a sterol regulatory element that binds the transcription factors Ecm22p and Upc2p, where, upon binding of Ecm22p and Upc2p, transcription is activated. In some embodiments, the level of activity of one or more of HMGS, MK, and PMK is increased by increasing the activity of Ecm22p and Upc2p. Vik et al. (2001) Mol. Cell. Biol. 19:6395-405.

Normally *S. cerevisiae* does not take up sterols from the environment under aerobic conditions. Lewis et al. ((1988) Yeast 4:93-106) isolated a yeast mutant, upc2-1 (uptake control), which resulted in aerobic sterol uptake. The upc2-1 allele comprises a guanine to adenine transition in the open reading frame designated YDR213W on chromosome IV. Crowley et al. (1998) J. Bacteriol. 16: 4177-4183. The nucleic acid sequence of wild-type Upc2 is known and can be obtained through GenBank Accession No. 268194. This wild-type allele is noted as coordinates 889746-892487 on the S. cerevisiae chromosome. As previously found by Lewis et al., under native conditions the level of sterol uptake was 10- to 20-fold greater than with the isogenic wild type. The mutant resulted in an increased ergosterol production.

The single amino acid change near the C-termini of Upc2p and Ecm22p transcription factors has been shown to increase their activity. In many embodiments, a subject genetically modified host cell is genetically modified such that Upc2p comprises a glycine-to-aspartic acid substitution at amino acid 888; and Ecm22p comprises a glycine-to-aspartic acid substitution at amino acid 790.

Increased Level of Prenyltransferase Activity

In some embodiments, a subject genetically modified eukaryotic host cell is genetically modified such that the level of geranyl diphosphate synthase (GPPS) and/or farnesyl diphosphate synthase (FPPS) activity is increased.

The enzyme farnesyl diphosphate synthase (FPPS) catalyzes a reaction that converts geranyl diphosphate (GPP) into farnesyl diphosphate (FPP). This step has also been shown to be rate limiting in the mevalonate pathway. Thus, FPPS is a point of regulation in organisms that naturally utilize the mevalonate pathway to produce isoprenoids. As such, and for ease of further description, modulating levels of activity of a prenyl transferase is discussed in terms of modulating the level of activity of a FPPS.

In some embodiments, the level of FPPS activity is increased. The level of FPPS activity in a genetically modified host cell can be increased in a number of ways, including, but not limited to, 1) increasing the promoter strength of the promoter to which the FPPS coding region is operably linked; 2) increasing the copy number of the plasmid comprising a nucleotide sequence encoding FPPS; 3) increasing the stability of an FPPS mRNA (where an "FPPS mRNA" is an mRNA comprising a nucleotide sequence encoding FPPS); 4) modifying the sequence of the ribosome binding site of an FPPS mRNA such that the level of translation of the FPPS mRNA is increased; 5) modifying the sequence between the ribosome binding site of an FPPS mRNA and the start codon of the FPPS coding sequence such that the level of translation of the FPPS mRNA is increased; 6) modifying the entire intercistronic region 5' of the start codon of the FPPS coding region such that translation of the FPPS mRNA is increased; 7) modifying the codon usage of FPPS such that the level of translation of the FPPS mRNA is increased, 8) expressing rare codon tRNAs used in FPPS such that the level of translation of the FPPS mRNA is increased; 9) increasing the enzyme stability of FPPS; or 10) increasing the specific activity (units activity per unit protein) of FPPS. The foregoing modifications may be made singly or in combination; e.g., two or more of the foregoing modifications may be made to provide for an increased level of FPPS activity.

Decreased Level of Squalene Synthase Activity

The enzyme squalene synthase catalyzes a reaction that converts farnesyl diphosphate into squalene. This step is the first step in the pathway leading from farnesyl diphosphate to ergosterol. Thus by limiting the action of this enzyme, FPP is shunted towards terpenoid production pathways utilizing, e.g., terpene synthases or GGPP synthase and subsequent terpene synthases.

In some embodiments, a subject genetically modified host cell is genetically modified such that the level of squalene synthase activity is decreased. The level of squalene synthase activity in the genetically modified host cell can be decreased in a number of ways, including, but not limited to, 1) decreasing the promoter strength of the promoter to which the squalene synthase coding region is operably linked; 2) decreasing the stability of an squalene synthase mRNA (where a "squalene synthase mRNA" is an mRNA comprising a nucleotide sequence encoding squalene synthase); 3) modifying the sequence of the ribosome binding site of a squalene synthase mRNA such that the level of translation of the squalene synthase mRNA is decreased; 4) modifying the sequence between the ribosome binding site of a squalene synthase mRNA and the start codon of the squalene synthase coding sequence such that the level of translation of the squalene synthase mRNA is decreased; 5) modifying the entire intercistronic region 5' of the start codon of the squalene synthase coding region such that translation of the squalene synthase mRNA is decreased; 6) modifying the codon usage of squalene synthase such that the level of translation of the squalene synthase mRNA is decreased, 7) decreasing the enzyme stability of squalene synthase; 8) decreasing the specific activity (units activity per unit protein) of squalene synthase, or 9) using a chemically-repressible-promoter and repressing the chemically-repressible-promoter by adding a chemical to a growth medium. The foregoing modifications may be made singly or in combination; e.g., two or more of the foregoing modifications may be made to provide for a decreased level of squalene synthase activity.

In an exemplary embodiment, the activity of squalene synthase in $S.$ $cerevisiae$ has been reduced or eliminated. Yeast ERG9 mutants that are unable to convert mevalonate into squalene have been produced. See, e.g., Karst et al. (1977) Molec. Gen. Genet. 154:269-277; U.S. Pat. No. 5,589,372; and U.S. Patent Publication No. 2004/0110257. Genetic modifications include decreasing the activity of squalene synthase by blocking or reducing the production of squalene synthase, reducing the activity of squalene synthase, or by inhibiting the activity of squalene synthase. Blocking or reducing the production of squalene synthase can include placing the squalene synthase gene under the control of a promoter that requires the presence of an inducing compound in the growth medium. By establishing conditions such that the inducer becomes depleted from the medium, the expression of squalene synthase can be turned off. Some promoters are turned off by the presence of a repressing compound. E.g., the promoters from the yeast CTR3 or CTR1 genes can be repressed by addition of copper. Blocking or reducing the activity of squalene synthase can include excision technology similar to that described in U.S. Pat. No. 4,743,546, incorporated herein by reference. In this approach the ERG9 gene is cloned between specific genetic sequences that allow specific, controlled excision of the ERG9 gene from the genome. Excision could be prompted by, e.g., a shift in the cultivation temperature of the culture, as in U.S. Pat. No. 4,743,546, or by some other physical or nutritional signal. Such a genetic modification includes any type of modification and specifically includes modifications made by recombinant technology and by classical mutagenesis. Inhibitors of squalene synthase are known (see U.S. Pat. No. 4,871,721 and the references cited in U.S. Pat. No. 5,475,029) and can be added to cell cultures.

In some embodiments, the codon usage of a squalene synthase coding sequence is modified such that the level of translation of the ERG9 mRNA is decreased. Reducing the level of translation of ERG9 mRNA by modifying codon usage is achieved by modifying the sequence to include codons that are rare or not commonly used by the host cell. Codon usage tables for many organisms are available that summarize the percentage of time a specific organism uses a specific codon to encode for an amino acid. Certain codons are used more often than other, "rare" codons. The use of "rare" codons in a sequence generally decreases its rate of translation. Thus, e.g., the coding sequence is modified by introducing one or more rare codons, which affect the rate of translation, but not the amino acid sequence of the enzyme translated. For example, there are 6 codons that encode for arginine: CGT, CGC, CGA, CGG, AGA, and AGG. In $E.$ $coli$ the codons CGT and CGC are used far more often (encoding approximately 40% of the arginines in $E.$ $coli$ each) than the codon AGG (encoding approximately 2% of the arginines in $E.$ $coli$). Modifying a CGT codon within the sequence of a gene to an AGG codon would not change the sequence of the enzyme, but would likely decrease the gene's rate of translation.

Generating a Genetically Modified Host Cell

A subject genetically modified host cell is generated using standard methods well known to those skilled in the art. In some embodiments, a heterologous nucleic acid comprising a nucleotide sequence encoding a variant mevalonate pathway enzyme and/or a heterologous nucleic acid comprising a nucleotide sequence encoding a variant transcription factor that controls transcription of a mevalonate pathway enzyme(s) is introduced into a host cell and replaces all or a part of an endogenous gene, e.g., via homologous recombination. In some embodiments, a heterologous nucleic acid is introduced into a parent host cell, and the heterologous nucleic acid recombines with an endogenous nucleic acid encoding a mevalonate pathway enzyme, a prenyltransferase, a transcription factor that controls transcription of one or more mevalonate pathway enzymes, or a squalene synthase, thereby genetically modifying the parent host cell.

In some embodiments, the heterologous nucleic acid comprises a promoter that has increased promoter strength compared to the endogenous promoter that controls transcription of the endogenous prenyltransferase, and the recombination event results in substitution of the endogenous promoter with the heterologous promoter. In other embodiments, the heterologous nucleic acid comprises a nucleotide sequence encoding a truncated HMGR that exhibits increased enzymatic activity compared to the endogenous HMGR, and the recombination event results in substitution of the endogenous HMGR coding sequence with the heterologous HMGR coding sequence. In some embodiments, the heterologous nucleic acid comprises a promoter that provides for regulated transcription of an operably linked squalene synthase coding sequence and the recombination event results in substitution of the endogenous squalene synthase promoter with the heterologous promoter.

Further Genetic Modifications

In some embodiments, a subject genetically modified host cell comprises one or more genetic modifications in addition to those discussed above. For example, in some embodiments, a subject genetically modified host cell is further genetically modified with one or more nucleic acids comprising nucleotide sequences encoding one or more of a prenyltransferase (e.g., a prenyltransferase other than FPP and GPP); a terpene synthase; and the like.

Codon Usage

In some embodiments, the nucleotide sequence encoding a gene product (e.g., a prenyltransferase, a terpene synthase, etc.) is modified such that the nucleotide sequence reflects the codon preference for the particular host cell. For example, the nucleotide sequence will in some embodiments be modified for yeast codon preference. See, e.g., Bennetzen and Hall (1982)J. Biol. Chem. 257(6): 3026-3031.

As noted above, in some embodiments, the codon usage of a squalene synthase coding sequence is modified such that the level of translation of the ERG9 mRNA is decreased. Reducing the level of translation of ERG9 mRNA by modifying codon usage is achieved by modifying the sequence to include codons that are rare or not commonly used by the host cell. Codon usage tables for many organisms are available that summarize the percentage of time a specific organism uses a specific codon to encode for an amino acid. Certain codons are used more often than other, "rare" codons. The use of "rare" codons in a sequence generally decreases its rate of translation. Thus, e.g., the coding sequence is modified by introducing one or more rare codons, which affect the rate of translation, but not the amino acid sequence of the enzyme translated. For example, there are 6 codons that encode for arginine: CGT, CGC, CGA, CGG, AGA, and AGG. In *E. coli* the codons CGT and CGC are used far more often (encoding approximately 40% of the arginines in *E. coli* each) than the codon AGG (encoding approximately 2% of the arginines in *E. coli*). Modifying a CGT codon within the sequence of a gene to an AGG codon would not change the sequence of the enzyme, but would likely decrease the gene's rate of translation.

Increased Acetyl-Coa Supply

Since acetyl-CoA is a reactant used by both acetoacetyl-CoA thiolase and HMGS in the MEV pathway, in some host cells, increases in the intracellular pool of acetyl-CoA could lead to increases in isoprenoid and isoprenoid precursors. Modifications that would increase the levels of intracellular acetyl-CoA include, but are not limited to, modifications that would decrease the total activity of lactate dehydrogenase within the cell, modifications that would decrease the total activity of acetate kinase within the cell, modifications that would decrease the total activity of alcohol dehydrogenase within the cell, modifications that would interrupt the tricarboxylic acid cycle, such as those that would decrease the total activity of 2-ketoglutarate dehydrogenase, or modifications that would interrupt oxidative phosphorylation, such as those that would decrease the total activity of the (F1F0) H+-ATP synthase, or combinations thereof.

Prenyltransferases

Prenyltransferases constitute a broad group of enzymes catalyzing the consecutive condensation of IPP resulting in the formation of prenyl diphosphates of various chain lengths. Suitable prenyltransferases include enzymes that catalyze the condensation of IPP with allylic primer substrates to form isoprenoid compounds with from about 5 isoprene units to about 6000 isoprene units or more, e.g., from about 5 isoprene units to about 10 isoprene units, from about 10 isoprene units to about 15 isoprene units, from about 15 isoprene units to about 20 isoprene units, from about 20 isoprene units to about 25 isoprene units, from about 25 isoprene units to about 30 isoprene units, from about 30 isoprene units to about 40 isoprene units, from about 40 isoprene units to about 50 isoprene units, from about 50 isoprene units to about 100 isoprene units, from about 100 isoprene units to about 250 isoprene units, from about 250 isoprene units to about 500 isoprene units, from about 500 isoprene units to about 1000 isoprene units, from about 1000 isoprene units to about 2000 isoprene units, from about 2000 isoprene units to about 3000 isoprene units, from about 3000 isoprene units to about 4000 isoprene units, from about 4000 isoprene units to about 5000 isoprene units, or from about 5000 isoprene units to about 6000 isoprene units or more.

Suitable prenyltransferases include, but are not limited to, an E-isoprenyl diphosphate synthase, including, but not limited to, geranylgeranyl diphosphate (GGPP) synthase, hexaprenyl diphosphate (HexPP) synthase, heptaprenyl diphosphate (HepPP) synthase, octaprenyl (OPP) diphosphate synthase, solanesyl diphosphate (SPP) synthase, decaprenyl diphosphate (DPP) synthase, chicle synthase, and gutta-percha synthase; and a Z-isoprenyl diphosphate synthase, including, but not limited to, nonaprenyl diphosphate (NPP) synthase, undecaprenyl diphosphate (UPP) synthase, dehydrodolichyl diphosphate synthase, eicosaprenyl diphosphate synthase, natural rubber synthase, and other Z-isoprenyl diphosphate synthases.

The nucleotide sequences of numerous prenyltransferases from a variety of species are known, and can be used or modified for use in generating a subject genetically modified eukaryotic host cell. Nucleotide sequences encoding prenyltransferases are known in the art.

See, e.g., Human farnesyl pyrophosphate synthetase mRNA (GenBank Accession No. J05262; Homo sapiens); farnesyl diphosphate synthetase (FPP) gene (GenBank Accession No. J05091; *Saccharomyces cerevisiae*); isopentenyl diphosphate:dimethylallyl diphosphate isomerase gene (J05090; *Saccharomyces cerevisiae*); Wang and Ohnuma (2000) Biochim. Biophys. Acta 1529:33-48; U.S. Pat. No. 6,645,747; *Arabidopsis thaliana* farnesyl pyrophosphate synthetase 2 (FPS2) / FPP synthetase 2 / farnesyl diphosphate synthase 2 (At4g17190) mRNA (GenBank Accession No. NM_202836); Ginkgo biloba geranylgeranyl diphosphate synthase (ggpps) mRNA (GenBank Accession No. AY371321); Arabidopsis thaliana geranylgeranyl pyrophosphate synthase (GGPS1) / GGPP synthetase / farnesyltranstransferase (At4g36810) mRNA (GenBank Accession No. NM_119845); Synechococcus elongatus gene for farnesyl, geranylgeranyl, geranylfarnesyl, hexaprenyl, heptaprenyl diphosphate synthase (SelF-HepPS) (GenBank Accession No. AB016095); etc.

In many embodiments, a eukaryotic host cell is genetically modified with a nucleic acid comprising a prenyltransferase. For example, in many embodiments, a host cell is genetically modified with a nucleic acid comprising nucleotide sequences encoding a prenyltransferase selected from a GGPP synthase, a GFPP synthase, a HexPP synthase, a HepPP synthase, an OPP synthase, an SPP synthase, a DPP synthase, an NPP synthase, and a UPP synthase.

Terpene Synthases

Terpene synthases catalyze the production of isoprenoid compounds via one of the most complex reactions known in chemistry or biology. In general, terpene synthases are moderately sized enzymes having molecular weights of about 40 to 100 kD. As an enzyme, terpene synthases can be classified as having low to moderate turnover rates coupled with exquisite reaction specificity and preservation of chirality. Turnover comprises binding of substrate to the enzyme, establishment of substrate conformation, conversion of substrate to product and product release. Reactions can be performed in vitro in aqueous solvents, typically require magnesium ions as cofactors, and the resulting products, which are often highly hydrophobic, can be recovered by partitioning into an organic solvent. U.S. Pat. No. 6,890,752.

In some embodiments, a subject genetically modified host cell is further genetically modified with a nucleic acid comprising a nucleotide sequence encoding a terpene synthase. In some embodiments, a nucleic acid with which a host cell is genetically modified comprises a nucleotide sequence encoding a terpene synthase that differs in amino acid sequence by one or more amino acids from a naturally-occurring terpene synthase or other parent terpene synthase, e.g., a variant terpene synthase. A "parent terpene synthase" is a terpene synthase that serves as a reference point for comparison. Variant terpene synthases include consensus terpene synthases and hybrid terpene synthases. In some embodiments, the synthetic nucleic acid comprises a nucleotide sequence encoding a consensus terpene synthase. In other embodiments, the synthetic nucleic acid comprises a nucleotide sequence encoding a hybrid terpene synthase.

A nucleic acid comprising a nucleotide sequence encoding any known terpene synthase can be used. Suitable terpene synthases include, but are not limited to, amorpha-4,11-diene synthase (ADS), beta-a synthase, germacrene A synthase, 8-epicedrol synthase, valencene synthase, (+)-delta-cadinene synthase, germacrene C synthase, (E)-beta-farnesene synthase, Casbene synthase, a synthase, 5-epi-aristolochene synthase, Aristolchene synthase, beta-caryophyllene, alpha-humulene, (E,E)-alpha-farnesene synthase, (−)-beta-pinene synthase, Gamma-terpinene synthase, limonene cyclase, Linalool synthase,1,8-cineole synthase, (+)-sabinene synthase, E-alpha-bisabolene synthase, (+)-bornyl diphosphate synthase, levopimaradiene synthase, Abietadiene synthase, isopimaradiene synthase,(E)-gamma-bisabolene synthase, taxadiene synthase, copalyl pyrophosphate synthase, kaurene synthase, longifolene synthase, gamma-humulene synthase, Delta-selinene synthase, beta-phellandrene synthase, limonene synthase, myrcene synthase, terpinolene synthase, (−)-camphene synthase, (+)-3-carene synthase, syn-copalyl diphosphate synthase, alpha-terpineol synthase, syn-pimara-7,15-diene synthase, ent-sandaaracopimaradiene synthase, sterner-13-ene synthase, E-beta-ocimene, S-linalool synthase, geraniol synthase, gamma-terpinene synthase, linalool synthase, E-beta-ocimene synthase, epi-cedrol synthase, alpha-zingiberene synthase, guaiadiene synthase, cascarilladiene synthase, cis-muuroladiene synthase, aphidicolan-16b-ol synthase, elizabethatriene synthase, sandalol synthase, patchoulol synthase, Zinzanol synthase, cedrol synthase, scareol synthase, copalol synthase, manool synthase, and the like.

Nucleotide sequences encoding terpene synthases are known in the art, and any known terpene synthase-encoding nucleotide sequence can used to genetically modify a host cell. For example, the following terpene synthase-encoding nucleotide sequences, followed by their GenBank accession numbers and the organisms in which they were identified, are known and can be used: (−)-germacrene D synthase mRNA (AY438099; *Populus balsamifera* subsp. *trichocarpa* ×*Populus deltoids*); E,E-alpha-farnesene synthase mRNA (AY640154; *Cucumis sativus*); 1,8-cineole synthase mRNA (AY691947; *Arabidopsis thaliana*); terpene synthase 5 (TPS5) mRNA (AY518314; Zea mays); terpene synthase 4 (TPS4) mRNA (AY518312; Zea mays); myrceneiocimene synthase (TPS10) (At2g24210) mRNA (NM_127982; *Arabidopsis thaliana*); geraniol synthase (GES) mRNA (AY362553; *Ocimum basilicum*); pinene synthase mRNA (AY237645; *Picea sitchensis*); myrcene synthase 1e20 mRNA (AY195609; *Antirrhinum majus*); (E)-β-ocimene synthase (0e23) mRNA (AY195607; *Antirrhinum majus*); E-μ-ocimene synthase mRNA (AY151086; *Antirrhinum majus*); terpene synthase mRNA (AF497492; *Arabidopsis thaliana*); (−)-camphene synthase (AG6.5) mRNA (U87910; *Abies grandis*); (−)-4S-limonene synthase gene (e.g., genomic sequence) (AF326518; *Abies grandis*); delta-selinene synthase gene (AF326513; Abies grandis); amorpha-4,11-diene synthase mRNA (AJ251751; Artemisia annua); E-α-bisabolene synthase mRNA (AF006195; *Abies grandis*); gamma-humulene synthase mRNA (U92267; Abies grandis); 8-selinene synthase mRNA (U92266; *Abies grandis*); pinene synthase (AG3.18) mRNA (U87909; *Abies grandis*); myrcene synthase (AG2.2) mRNA (U87908; *Abies grandis*); etc.

Amino acid sequences of the following terpene synthases are found under the GenBank Accession numbers shown in parentheses, along with the organism in which each was identified, following each terpene synthase: (−)-germacrene D synthase (AAR99061; *Populus balsamifera* subsp. *trichocarpa* ×*Populus deltoids*); D-cadinene synthase (P93665; *Gossypium hirsutum*); 5-epi-aristolochene synthase (Q40577; Nicotiana tabacum); E,E-alpha-farnesene synthase (AAU05951; *Cucumis sativus*); 1,8-cineole synthase (AAU01970; *Arabidopsis thaliana*); (R)-limonene synthase 1 (Q8L5K3; Citrus limon); syn-copalyl diphosphate synthase (AAS98158; Oryza sativa); a taxadiene synthase (Q9FT37; Taxus chinensis; Q93YA3; Taxus bacca; Q41594; Taxus brevifolia); a D-cadinene synthase (Q43714; *Gossypium arboretum*); terpene synthase 5 (AAS88575; Zea mays); terpene synthase 4 (AAS88573; Zea mays); terpenoid synthase (AAS79352; Vitis vinifera); geraniol synthase (AAR11765; Ocimum basilicum); myrcene synthase 1e20 (AA041727; *Antirrhinum majus*); 5-epi-aristolochene synthase 37 (AAP05762; Nicotiana attenuata); (+)-3-carene synthase (AA073863; Picea abies); (−)-camphene synthase (AAB70707; *Abies grandis*); abietadiene synthase (AAK83563; *Abies grandis*); amorpha-4,11-diene synthase (CAB94691; Artemisia annua); trichodiene synthase (AAC49957; Myrothecium roridum); gamma-humulene synthase (AAC05728; Abies grandis); δ-selinene synthase (AAC05727; Abies grandis); etc.

Nucleic Acids, Vectors, Promoters

To generate a genetically modified host cell, one or more nucleic acids comprising nucleotide sequences encoding one or more gene products is introduced stably or transiently into a host cell, using established techniques, including, but not limited to, electroporation, calcium phosphate precipitation, DEAE-dextran mediated transfection, liposome-mediated transfection, heat shock in the presence of lithium acetate, and the like. For stable transformation, a nucleic acid will generally further include a selectable marker, e.g., any of several well-known selectable markers such as neomycin resistance, ampicillin resistance, tetracycline resistance, chloramphenicol resistance, kanamycin resistance, and the like.

In many embodiments, the nucleic acid with which the host cell is genetically modified is an expression vector that includes a nucleic acid comprising a nucleotide sequence that encodes a gene product, e.g., a mevalonate pathway enzyme, a transcription factor, a prenyltransferase, a terpene synthase, etc. Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors specific for specific hosts of interest (such as yeast). Thus, for example, a nucleic acid encoding a gene product(s) is included in any one of a variety of expression vectors for expressing the gene product(s). Such vectors include chromosomal, nonchromosomal and synthetic DNA sequences.

Numerous suitable expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other plasmid or other vector may be used so long as it is compatible with the host cell.

The nucleotide sequence in the expression vector is operably linked to an appropriate expression control sequence(s) (promoter) to direct synthesis of the encoded gene product. Depending on the host/vector system utilized, any of a number of suitable transcription and translation control elements, including constitutive and inducible promoters, transcription enhancer elements, transcription terminators, etc. may be used in the expression vector (see, e.g., Bitter et al. (1987) Methods in Enzymology, 153:516-544).

Non-limiting examples of suitable eukaryotic promoters (promoters that are functional in eukaryotic cells) include CMV immediate early, HSV thymidine kinase, early and late SV40, LTRs from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

In addition, the expression vectors will in many embodiments contain one or more selectable marker genes to provide a phenotypic trait for selection of transformed host cells such as dihydrofolate reductase or neomycin resistance for eukaryotic cell culture.

Generally, recombinant expression vectors will include origins of replication and selectable markers permitting transformation of the host cell, e.g., the S. cerevisiae TRP1 gene, etc.; and a promoter derived from a highly-expressed gene to direct transcription of the gene product-encoding sequence. Such promoters can be derived from operons encoding glycolytic enzymes such as 3-phosphoglycerate kinase (PGK), α-factor, acid phosphatase, or heat shock proteins, among others.

In many embodiments, a genetically modified host cell is genetically modified with a nucleic acid that includes a nucleotide sequence encoding a gene product, where the nucleotide sequence encoding the gene product is operably linked to an inducible promoter. Inducible promoters are well known in the art. Suitable inducible promoters include, but are not limited to, the pL of bacteriophage λ; Plac; Ptrp; Ptac (Ptrp-lac hybrid promoter); an isopropyl-beta-D-thiogalactopyranoside (IPTG)-inducible promoter, e.g., a lacZ promoter; a tetracycline-inducible promoter; an arabinose inducible promoter, e.g., PBAD (see, e.g., Guzman et al. (1995) J. Bacteriol. 177:4121-4130); a xylose-inducible promoter, e.g., Pxyl (see, e.g., Kim et al. (1996) Gene 181:71-76); a GAL1 promoter; a tryptophan promoter; a lac promoter; an alcohol-inducible promoter, e.g., a methanol-inducible promoter, an ethanol-inducible promoter; a raffinose-inducible promoter; a heat-inducible promoter, e.g., heat inducible lambda PL promoter, a promoter controlled by a heat-sensitive repressor (e.g., 0857-repressed lambda-based expression vectors; see, e.g., Hoffmann et al. (1999) FEMS Microbiol Lett. 177(2):327-34); and the like.

In many embodiments, a genetically modified host cell is genetically modified with a nucleic acid that includes a nucleotide sequence encoding a gene product, where the nucleotide sequence encoding the gene product is operably linked to a constitutive promoter. In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp.516-544; Glover, 1986, DNA Cloning, Vol. II, IRL Press, Wash., D.C., Ch. 3; Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast Saccharomyces, 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein in: DNA Cloning Vol. 11, A Practical Approach, Ed. DM Glover, 1986, IRL Press, Wash., D.C.). Alternatively, vectors may be used which promote integration of foreign DNA sequences into the yeast chromosome.

Compositions Comprising a Subject Genetically Modified Eukaryotic Host Cell

The present invention further provides compositions comprising a subject genetically modified eukaryotic host cell. A subject composition comprises a subject genetically modified eukaryotic host cell, and will in some embodiments comprise one or more further components, which components are selected based in part on the intended use of the genetically modified eukaryotic host cell. Suitable components include, but are not limited to, salts; buffers; stabilizers; protease-inhibiting agents; cell membrane- and/or cell wall-preserving compounds, e.g., glycerol, dimethylsulfoxide, etc.; nutritional media appropriate to the cell; and the like.

Methods for Producing Isoprenoid Compounds

The present invention provides methods of producing an isoprenoid or an isoprenoid precursor compound. The methods generally involve culturing a subject genetically modified host cell in a suitable medium.

Isoprenoid precursor compounds that can be produced using a subject method include any isoprenyl diphosphate compound. Isoprenoid compounds that can be produced using the method of the invention include, but are not limited to, monoterpenes, including but not limited to, limonene, citranellol, geraniol, menthol, perillyl alcohol, linalool, thujone; sesquiterpenes, including but not limited to, periplanone B, gingkolide B, amorphadiene, artemisinin, artemisinic acid, valencene, nootkatone, epi-cedrol, epi-aristolochene, farnesol, gossypol, sanonin, periplanone, and forskolin; diterpenes, including but not limited to, casbene, eleutherobin, paclitaxel, prostratin, and pseudopterosin; and triterpenes, including but not limited to, arbrusideE, bruceantin, testosterone, progesterone, cortisone, digitoxin. Isoprenoids also include, but are not limited to, carotenoids such as lycopene, α- and β-carotene, α- and β-cryptoxanthin, bixin, zeaxanthin, astaxanthin, and lutein. Isoprenoids also include, but are not limited to, triterpenes, steroid compounds, and compounds that are composed of isoprenoids modified by other chemical groups, such as mixed terpene-alkaloids, and coenzyme Q-10.

In some embodiments, a subject method further comprises isolating the isoprenoid compound from the cell and/or from the culture medium.

In general, a subject genetically modified host cell is cultured in a suitable medium (e.g., Luria-Bertoni broth, optionally supplemented with one or more additional agents, such as an inducer (e.g., where one or more nucleotide sequences encoding a gene product is under the control of an inducible promoter), etc.). In some embodiments, a subject genetically modified host cell is cultured in a suitable medium; and the culture medium is overlaid with an organic solvent, e.g., dodecane, forming an organic layer. The isoprenoid compound produced by the genetically modified host cell partitions into the organic layer, from which it can be purified. In some embodiments, where one or more gene product-encoding nucleotide sequence is operably linked to an inducible promoter, an inducer is added to the culture medium; and, after a suitable time, the isoprenoid compound is isolated from the organic layer overlaid on the culture medium.

In some embodiments, the isoprenoid compound will be separated from other products which may be present in the organic layer. Separation of the isoprenoid compound from other products that may be present in the organic layer is readily achieved using, e.g., standard chromatographic techniques.

In some embodiments, the isoprenoid compound is pure, e.g., at least about 40% pure, at least about 50% pure, at least about 60% pure, at least about 70% pure, at least about 80% pure, at least about 90% pure, at least about 95% pure, at least about 98% pure, or more than 98% pure, where "pure" in the context of an isoprenoid compound refers to an isoprenoid compound that is free from other isoprenoid compounds, contaminants, etc.

EXAMPLES

The following examples are put forth so as to provide those of ordinary skill in the art with a complete disclosure and description of how to make and use the present invention, and are not intended to limit the scope of what the inventors regard as their invention, nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Producing High Levels Of An Isoprenoid Compound In A Genetically Modified Yeast Cell Materials and Methods Chemicals. Dodecane and caryophyllene were purchased from Sigma-Aldrich (St. Louis, Mo.). 5-fluoortic acid (5-FOA) was purchased from Zymo Research (Orange, Calif.). Complete Supplement Mixtures for formulation of Synthetic Defined media were purchased from Qbiogene (Irvine, Calif,). All other media components were purchased from either Sigma-Aldrich or Becton, Dickinson (Franklin Lakes, N.J.).

Strains and media. Escherichia coli strains DH10B and DH5α were used for bacterial transformation and plasmid amplification in the construction of the expression plasmids used in this study. The strains were cultivated at 37° C. in Luria-Bertani medium with 100 mg liter$^{-1}$ ampicillin with the exception of pδ-UB based plasmids which were cultivated with 50 mg liter$^{-1}$ ampicillin.

Saccharomyces cerevisiae strain BY4742 (Baker Brachmann et al. (1998) Yeast 14(2):115-132), a derivative of S288C, was used as the parent strain for all yeast strains. This strain was grown in rich YPD medium. Burke et al. Methods in yeast genetics: a Cold Spring Harbor laboratory course manual. 2000, Plainview, NY: Cold Spring Harbor Laboratory Press. Engineered yeast strains were grown in Synthetic Defined medium (SD) (Burke et al. (2000) supra) with leucine, uracil, histidine, and/or methionine dropped out where appropriate. For induction of genes expressed from the GAL1 promoter, S. cerevisiae strains were grown in 2% galactose as the sole carbon source.

Plasmid construction. To create plasmid pRS425ADS for expression of ADS with the GAL1 promoter, ADS was amplified by polymerase chain reaction (PCR) from pADS (Martin et al. (2003) Nat. Biotechnol. 21(7): p. 796-802) using primer pair ADS-SpeI-F/ADS-HindIII-R (Table 1). Using these primers, the nucleotide sequence 5'-AAAACA-3' was cloned immediately upstream of the start codon of ADS. This consensus sequence was used for efficient translation (Looman et al. (1993) Nucleic Acids Research. 21(18):4268-71; Yun et al. (1996) Molecular Microbiol. 19(6):1225-39.) of ADS and the other galactose-inducible genes used in this study. The amplified product was cleaved with SpaI and HindIII and cloned into SpeI and HindIII digested pRS425GAL1 (Mumberg et al. (1995) Gene 156 (1):119-122).

TABLE 1

| Primer | Sequence (5' to 3') |
|---|---|
| ADS-SpeI-F | GG<u>ACTAGT</u>AAAACAATGGCCCTGACCGAA GAG (SEQ ID NO: 3) |

TABLE 1-continued

| Primer | Sequence (5' to 3') |
|---|---|
| ADS-HindIII-R | CCAAGCTTTCAGATGGACATCGGGTAAAC (SEQ ID NO: 4) |
| HMGR-BamHI-F | CGGGATCCAAAACAATGGCTGCAGACCAATTGGTG (SEQ ID NO: 5) |
| HMGR-SalI-R | GCGTCGACTTAGGATTTAATGCAGGTGACG (SEQ ID NO: 6) |
| pRS42X-PvuIISacII-F | CTGCCGCGGGGCCGCAAATTAAAGCCTTC (SEQ ID NO: 7) |
| pRS42X-PvuIISacII-R | CTGCCGCGGTAGTACGGATTAGAAGCCGC (SEQ ID NO: 8) |
| UPC2-BamHI-F | CGGGATCCAAAACAATGAGCGAAGTCGGTATACAG (SEQ ID NO: 9) |
| UPC2-SalI-R | GCGTCGACTCATAACGAAAAATCAGAGAAATTTG (SEQ ID NO: 10) |
| ECM22-BamHI-R | CGGGATCCAAAACAATGACATCCGATGATGGGAATG (SEQ ID NO: 11) |
| ECM22-SalI-R | GCGTCGACTTACATAAAAGCTGAAAAGTTTGTAG (SEQ ID NO: 12) |

Restriction sites are underlined and bold indicates a start or stop codon.

For expression of tHMGR, plasmid pRS-HMGR was constructed. First SacII restriction sites were introduced into pRS426GAL1 (Mumberg et al. (1995) Gene 156(1):119-122) at the 5' end of the GAL1 promoter and 3' end of the CYCI terminator. The promoter-multiple cloning site-terminator cassette of pRS426GAL1 was PCR amplified using primer pair pRS42X-PvullSacII-F/pRS42X-PvullSacII-R (Table 1). The amplified product was cloned directly into PvuII digested pRS426GAL1 to construct vector pRS426-SacII. The catalytic domain of HildG1 was PCR amplified from plasmid pRH127-3 (Donald et al. (1997) Appl. Environ. Microbiol. 63(9):3341-44) with primer pair HMGR-BamHI-F/HMGR-SalI-R. The amplified product was cleaved with BamHI and SalI and cloned into BamHI and XhoI digested pRS426-SacII.

The upc2-1 allele of UPC2 was PCR amplified from plasmid pBD33 using primer pair UPC2-BamHI-F/UPC2-SalI-R. The amplified product was cleaved with BamHI and SalI and cloned into BamHI and XhoI digested pRS426-SacII to create plasmid pRS-UPC2. Likewise the ECM22 gene containing the upc2-1 like mutation (glycine to aspartate at residue 790) was PCR amplified from plasmid pBD36 using primer pair ECM22-BamHI-F/UPC2-SalI-R. The amplified product was cleaved with BamHI and SalI and cloned into BamHI and XhoI digested pRS426-SacII to create plasmid pRS-ECM22.

A plasmid was constructed for the integration of the tHMGR expression cassette of pRS-HMGR into the yeast genome utilizing plasmid pδ-UB (Lee et al. (1997) Biotechnol Prog. 13(4):368-373). pRS-HMGR was cleaved with SacII and the expression cassette fragment was gel extracted and cloned into SacII digested pδ-UB. For the integration of upc2-1, pδ-UPC2 was created in an identical manner by digesting pRS-UPC2 with SacII and moving the appropriate fragment to pδ-UB.

To replace the ERG9 promoter with the MET3 promoter, plasmid pRS-ERG9 was constructed. Plasmid pRH973 (Gardner et al. (1999) J. Biol. Chem. 274(44):31671-31678) contained a truncated 5' segment of ERG9 placed behind the MET3 promoter. pRH973 was cleaved with ApaI and ClaI and cloned into ApaI and ClaI digested pRS403 (Sikorski et al. (1989) Genetics, 122(1):19-27).

For expression of ERG20, plasmid pRS-ERG20 was constructed. Plasmid pRS-SacII was first digested with SalI and XhoI which created compatible cohesive ends. The plasmid was then self-ligated, eliminating SalI and XhoI sites to create plasmid pRS-SacII-DX. ERG20 was PCR amplified from the genomic DNA of BY4742 using primer pair ERG20-SpeI-F/ERG20-SmaI-R. The amplified product was cleaved with SpeI and SmaI and cloned into SpeI and SmaI digested pRS-SacII-DX. For the integration of the ERG20 expression cassette, pRS-ERG20 was cleaved with SacII and the expression cassette fragment was gel extracted and cloned into SacII digested pδ-UB.

A description of plasmids used in this study is provided in Table 2.

TABLE 2

| Name | Gene expressed | Plasmid status | Marker |
|---|---|---|---|
| pRS425ADS | ADS | 2-micron replicon | LEU2 |
| pRS-HMGR | tHMGR | 2-micron replicon | URA3 |
| pRS-UPC2 | upc2-1 | 2-micron replicon | URA3 |
| pRS-ECM22 | ECM22 (upc2-1 mutant) | 2-micron replicon | URA3 |
| pδ-HMGR | tHMGR | Integration | URA3 |
| pδ-UPC2 | upc2-1 | Integration | URA3 |
| pRS-ERG9 | $P_{MET3}$-ERG9 | Integration | HIS3 |
| pδ-ERG20 | ERG20 | Integration | URA3 |

A list of yeast strains used in this study, and the relevant genotypes of the strains, is provided in Table 3.

TABLE 3

| BY4742 | MATα his3Δ1 leu2Δ0 lys2Δ0 ura3Δ0 |
|---|---|
| EPY201 | BY4742 pRS425ADS |
| EPY203 | BY4742 pRS425ADS pRS-HMGR |
| EPY204 | BY4742 pRS425ADS pRS-UPC2 |
| EPY205 | BY4742 pRS425ADS pRS-ECM22 |
| EPY206 | BY4742 pRS425ADS pRS-ERG20 |
| EPY207 | BY4742 pRS425ADS tHMGR (ura+) |
| EPY209 | BY4742 pRS425ADS tHMGR upc2-1 (ura+) |
| EPY212 | BY4742 pRS425ADS tHMGR upc2-1 erg9::PMET3-ERG9 (ura+) |
| EPY214 | BY4742 pRS425ADS tHMGR upc2-1 erg9::PMET3-ERG9 ERG20 (ura+) |

Yeast transformation and strain construction. S. cerevisiae strain BY4742 (Carrie Baker Brachmann et al. (1998) "Yeast" 14(2):115-132), a derivative of S288C was used as the parent strain for all S. cerevisiae strains. Transformation of all strains of S. cerevisiae was performed by the standard lithium acetate method (Gietz et al. (2002) Guide to Yeast Genetics and Molecular and Cell Biology, Pt B., Academic Press Inc: San Diego. 87-96). Three to ten colonies from each transformation were screened for the selection of the highest amorphadiene producing transformant. Strain EPY201 was constructed by the transformation of strain BY4742 with plasmid pRS425ADS and selection on SD-LEU plates. Strains EPY203, EPY204, EPY205, and EPY206 were constructed by the transformation of strain EPY201 with plasmid pRS-HMGR, pRS-UPC2, pRS-ECM22, and pRS-ERG20, respectively. Transformants were selected on SD-LEU-URA plates. Plasmid pδ-HMGR was digested with XhoI before transformation of the DNA into strain EPY201 for the construction of EPY207. Strain EPY207 was cultured and plated on SD-LEU plates including 1 g/L 5-FOA selection of the loss of the URA3 marker. The resulting uracil auxotroph was then transformed with XhoI digested pδ-UPC2 plasmid DNA for the construction of EPY209, which was selected on SD-LEU-URA plates. Plasmid pRS-ERG9 was cleaved with HindII for the integration of the $P_{MET3}$-ERG9 fusion at the ERG9 loci of EPY209 for the construction of EPY212. This strain was selected for on SD-LEU-URA-HIS-MET plates. EPY212 was cultured and plated on SD-LEU-HIS-MET plates containing 5-FOA for selection of the loss of the URA3 marker. The resulting uracil auxotroph was then transformed with XhoI digested pδ-ERG20 plasmid DNA for the construction of EPY214, which was selected on SD-LEU-URA-HIS-MET plates.

Figure 4:
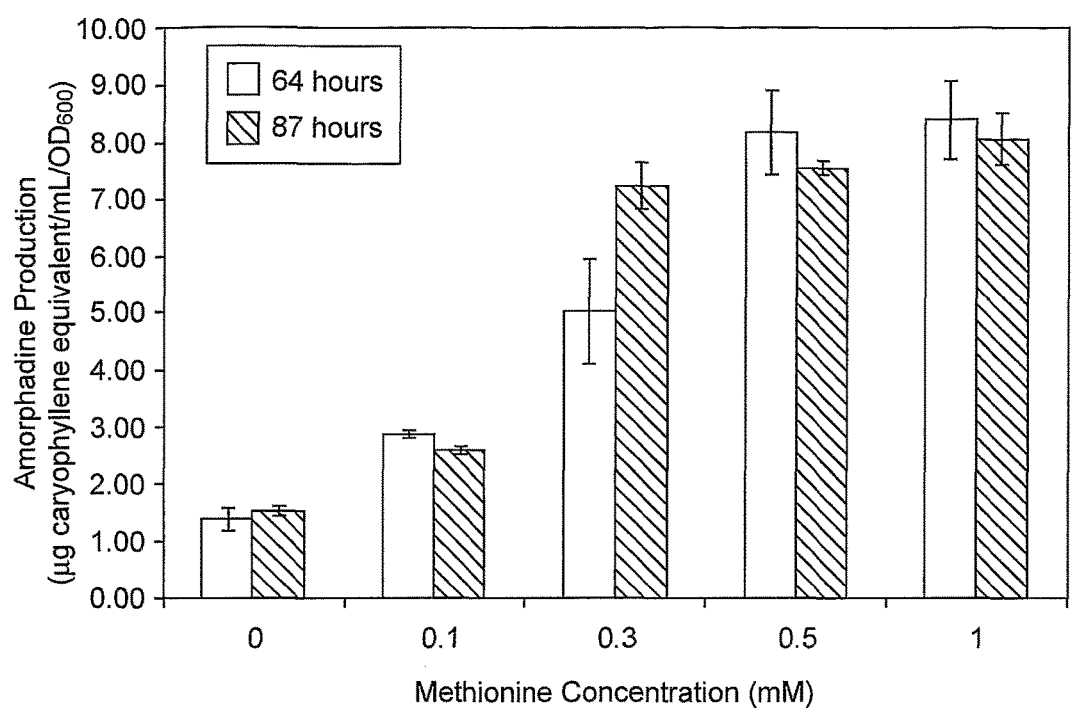
FIG. 4 depicts production of amorphadiene in S. cerevisiae strain EPY212 grown at methionine concentrations of 0, 0.1, 0.3, 0.5 and 1 after 64 and 87 hours of culture. The data are the means of means from two samples.

Yeast cultivation. For time course experiments for the measurement of amorphadiene production, culture tubes containing 5 mL of SD (2% galactose) media (with appropriate amino acid omissions as described above) were inoculated with the strains of interest. These innocula were grown at 30° C. to an optical density at 600 nm ($OD_{600}$) of approximately 1. 250 mL baffled flasks containing 50 mL SD media were inoculated to an $OD_{600}$ 0.05 with these seed cultures. FIG. 4. represents strains grown in SD-URA-LEU-HIS with methionine at the level indicated. Media for strains shown in FIG. 5 contained SD-URA supplemented with methionine to a final concentration of 1 mM. All other production experiments used SD-URA or SD-URA-LEU where appropriate.

All flasks also contained 5 mL dodecane. This dodecane layer was sampled and diluted in ethyl acetate for determination of amorphadiene production by GC-MS.

GC-MS analysis of amorphadiene. Amorphadiene production by the various strains was measured by GC-MS as previously described (Martin et al. (2001) Biotechnology and Bioengineering, 75(5):497-503) by scanning only for two ions, the molecular ion (204 m/z) and the 189 m/z ion. Amorphadiene concentrations were converted to caryophyllene equivalents using a caryophyllene standard curve and the relative abundance of ions 189 and 204 m/z to their total ions.

Results

To maximize production of amorphadiene, a step-wise approach was taken with the successive integration of constructs into the S. cerevisiae genome.

Production of amorphadiene. A platform host cell, S. cerevisiae, was engineered for high-level production of isoprenoids. S. cerevisiae directs all of its isoprenoid production through isopentenyl diphosphate (IPP), and most of this then through farnesyl diphosphate (FPP). The levels of IPP and FPP were increased in the host strain. IPP and FPP are metabolized to a variety of native products. Instead of measuring FPP levels, the level of amorphadiene, a direct product of FPP that will not be metabolized or degraded during the time course of growth, was measured. Amorphadiene synthase (ADS) was expressed in S. cerevisiae for the enzymatic cyclization of FPP to the sesquiterpene amorphadiene. Amorphadiene is also readily quantified by GCMS.

ADS was expressed on the 2-micron plasmid pRS425ADS under the inducible control of the GAL1 promoter. Cultures of S. cerevisiae were grown for six days on galactose for expression of ADS, and amorphadiene levels were measured every 24 hours. S. cerevisiae modified solely by the introduction of pRS425ADS reached a maximum amorphadiene production of 4.6 µg amorphadiene $mL^{-1}$ after four days (FIG. 3A).

Previous control experiments consisting of media spiked with pure amorphadiene showed the rapid loss of the sesquiterpene from the liquid phase. A layer of dodecane equivalent to 10% of the medium volume was added to each shaker flask to sequester the amorphadiene from the culture. The addition of this organic layer ensures accurate measurement of the total amount of amorphadiene produced by preventing loss to the air. The volatilization of amorphadiene is a particular problem during extended time courses of several days like those used in this study.

Overexpression of HMG-CoA reductase. The medical importance of the biosynthesis of cholesterol and the experimental ease of analysis in S. cerevisiae has made it an ideal organism for study of the regulation of the mevalonate pathway over the past decades (Szkopinska et al. (2000) Biochemical and Biophysical Research Communications, 267(1):473-477; Dimster-Denk et al. (1999) J. Lipid Res., 40(5):850-860).

These studies have elucidated a complex system of regulation, with 3-hydroxy-3-methylglutaryl-coenzyme A reductase (HMGR) as the major regulatory control point of the pathway. Two isozymes of HMGR, Hmg1p and Hmg2p, are present in yeast, with Hmg1p being the more stable of the two (Hampton et al. (1996) Trends in Biochemical Sciences, 21(4):140-145). Hmg1p is an integral membrane bound protein containing an N-terminal region responsible for anchoring the protein to the ER membrane (Liscum et al. (1985) J. Biol. Chem. 260(1):522-530). For expression of a soluble form of the enzyme (Donald et al. (1997) Appl. Environ. Microbiol. 63(9):3341-44) removed the membrane-bound N-terminus of Hmg1p and expressed only the catalytic domain. In our study, this truncated form of HMGR (tHMGR) on a 2-micron plasmid was expressed under the control of the GAL1 promoter. When expressed in conjunction with ADS, S. cerevisiae reached a maximal production of 11.2 µg amorphadiene $mL^{-1}$ after four days (FIG. 3A.).

Overexpression of sterol-involved transcription factors. In another approach to increase amorphadiene, two S. cerevisiae transcription factors previously identified for their importance in regulation of sterol biosynthesis were used. upc2-1 S. cerevisiae mutants were originally identified by their unique ability to uptake sterols under aerobic conditions (Lewis et al. (1988) Yeast, 4(2):93-106). Further characterization showed that these mutants had increased sterol synthesis capabilities (Lewis et al. (1988) Yeast, 4(2):93-106). The mutation responsible for these characteristics is a single guanine to adenine transition in the UPC2 gene; this point mutation results in a residue change from glycine to aspartate at amino acid 888 near the carboxy terminus (Crowley et al. (1998) J. Bacteriol., 180(16):4177-83). A homolog to this gene, ECM22, was later identified with 45% amino acid sequence identity (Shianna et al. (2001) J. Bacteria, 183(3):830-834). 36 amino acids are completely conserved between UPC2 and ECM22 at the locus of the upc2-1 point mutation (Shianna et al. (2001) J. BacterioL, 183(3):830-834). The upc2-1 point mutation was introduced into the wild type ECM22 allele resulting in a strain with a similar phenotype to that of the upc2-1 mutant (Shianna et al. (2001) J. BacterioL, 183(3):830-834).

Vik and Rine identified ERG2 and ERG3 as targets for gene regulation by Ecm22p and Upc2p. A 7 base pair sterol regulatory element was identified as the necessary binding location for these transcription factors. This 7 base pair sequence element is found in the promoters of many other sterol pathway genes including ERG8, ERG12, and ERG13

(Vik et al. (2001) Mol. Cell. Biol., 21(19):6395-6405.). The enzyme products for each of these three genes are involved in isoprenoid synthesis upstream of FPP (see FIG. 1).

It was hypothesized that coexpression of the mutant alleles for UPC2 and ECM22 with ADS would increase amorphadiene production by increasing metabolic flux through the mevalonate pathway. The upc2-1 mutant alleles of UPC2 and ECM22 were each expressed under the control of the GAL1 promoter on a 2-micron plasmid in a strain already harboring pRS425ADS. Absolute amorphadiene production in the cultures increased only minimally for UPC2 and ECM22 expression, in part due to decreased cell densities. However production normalized for cell density rose 76% and 53% for the expression of UPC2 and ECM22, respectively (FIG. 3B).

This relatively small increase in amorphadiene production compared to overexpression of tHMGR supports the fact that HMGR activity is the major limiting bottleneck of the mevalonate pathway. Even high-level expression of ERG8, ERG12, and ERG13 is unlikely to greatly enhance flux through the pathway if HMGR remains at basal expression level. The decreased cell densities observed for the overexpression of UPC2 and ECM22 is unlikely due to increased flux through the mevalonate pathway to FPP. It is instead likely caused by an unfavorable change in transcriptional regulation for one or multiple other genes controlled by UPC2 and ECM22.

Figure 5:
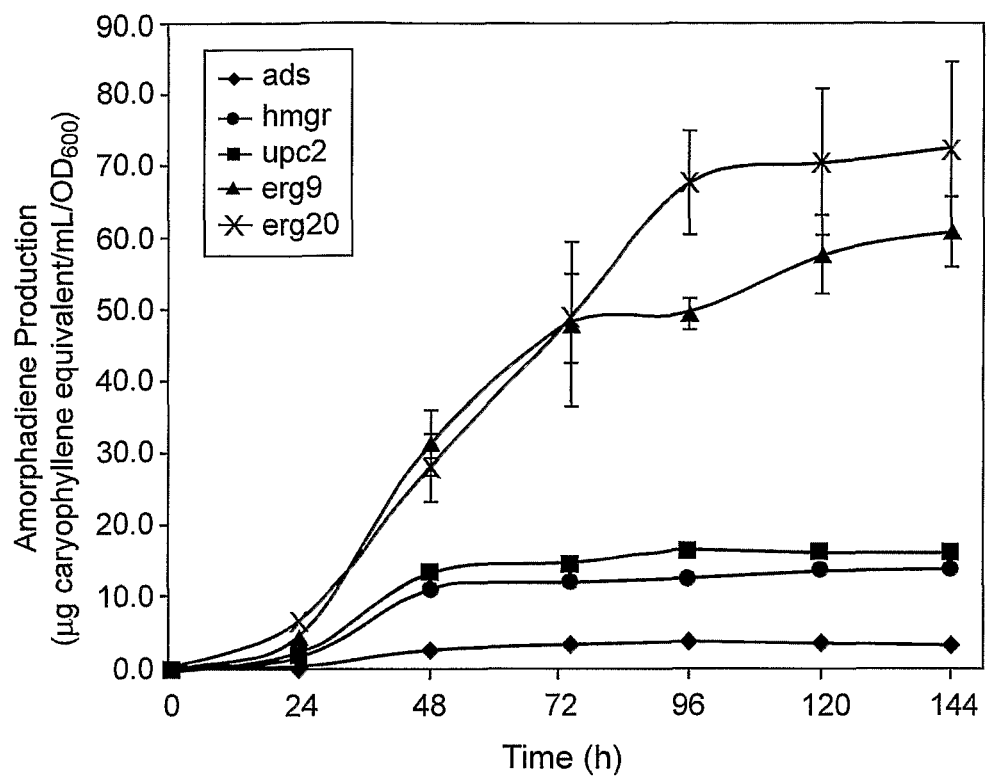
FIG. 5 depicts production of amorphadiene by S. cerevisiae by various yeast strains over 144 hours of culture expressing. The data are means ±standard deviations (n=3).

Coexpression of tHMGR and upc2-1. Overexpression of tHMGR and upc2-1 each increased the final yield of amorphadiene in the cell cultures. To test the possibility of a synergistic effect from the overexpression of these genes together, the expression cassettes were integrated sequentially into the S. cerevisiae genome. Plasmid pδ-UB (Lee et al. (1997) Biotechnol Prog., 13(4):368-373) was used for the construction of the integration plasmids. This plasmid contains a reusable URA3 Blaster Cassette allowing for recycling of the URA3 marker. Additionally, it integrates at a δ-sequence (found in the long terminal repeats of Ty-transposon sites), of which there are approximately 425 dispersed through the genome (Dujon (1996) Trends in Genetics, 12(7):263-270).

tHMGR was integrated into the chromosome of a strain harboring pRS425ADS using pδ-HMGR. The amorphadiene production level of 13.8 µg amorphadiene mL$^{-1}$ was comparable in this strain to strain EP203 which contained tHMGR on a high-copy plasmid (FIG. 5). After recycling the URA3 marker by plating on 5-FOA, upc2-1 was integrating into the chromosome using plasmid pδ-UPC2. The effects of overexpressing tHMGR and upc2-1 combined to raise amorphadiene production to 16.2 µg amorphadiene mL$^{-1}$ (FIG. 5). Although expression of upc2-1 in combination with tHMGR raised absolute amorphadiene production by 17%, this increase is only comparable to that seen when upc2-1 is expressed with ADS alone. With the removal of the HMGR bottleneck, we expected a more significant impact from upc2-1 expression. Potential increases in amorphadiene production might be prevented due to the routing of FPP to other metabolites.

Down-regulation of squalene synthase. The increases seen in amorphadiene production suggested an increased precursor pool of FPP. FPP is central to the synthesis of a number of S. cerevisiae compounds including sterols, dolichols and polyprenols, and prenylated proteins. Although increased flux through the mevalonate pathway lead to higher amorphadiene production, a number of other enzymes were also competing for the increased pool of FPP, most importantly squalene synthase encoded by ERG9.

Squalene synthesis is the branch-point from FPP leading to ergosterol. In a strain expressing the catalytic domain of HMGR and containing an ERG9 deletion, FPP was seen to accumulate (Song (2003) Analytical Biochemistry, 317(2): 180-185). With the aim of routing FPP away from the sterol production and toward amorphadiene production, reduction in squalene synthase activity would be useful. However, an ERG9 deletion is lethal without exogenous supplementation of sterols.

Employing an alternate strategy, ERG9 was transcriptionally down-regulated by replacing its native promoter with a methionine repressible promoter, $P_{MET3}$ (Cherest et al. (1985) Gene, 34(2-3):269-281). Gardner et al. previously utilized such a $P_{MET3}$-ERG9 fusion construct for the study of HMGR degradation signals (Gardner et a. (1999) J. Biol. Chem. 274(44):31671-31678; Gardner et al. (2001) J. Biol. Chem., 276(12):8681-8694). Plasmid pRS-ERG9 was constructed to utilize the same strategy as Gardner in the replacement of the ERG9 native promoter with the MET3 promoter. The utility of the $P_{MET3}$-ERG9 fusion is underscored by the tight regulatory control between 0 and 100 µM extracellular concentrations of methionine (Mao et al. (2002) Current Microbiology, 45(1):37-40). In the presence of the high extracellular concentrations of methionine, expression from the MET3 promoter is very low. After integration of pRS-ERG9 at the ERG9 locus, we could tune the squalene synthase expression based upon methionine supplementation to the medium.

pRS-ERG9 was integrated into strain EPY209, and amorphadiene production was measured with a range of 0 to 1 mM methionine in the medium. Time points of 64 and 87 hours after inoculation are shown (FIG. 4). The data suggests that minimal expression of ERG9 (methionine concentrations above 0.5 mM) maximize the production of amorphadiene. As the S. cerevisiae cultures increase in cell density and metabolize the nutrients in the medium, the methionine concentration likely drops, explaining why cultures provided with 0.1 mM methionine in the medium have lower yields of amorphadiene. 1 mM methionine was selected for future experiments to ensure high extracellular concentrations throughout the extended time courses.

Strain EPY212 containing an integrated copy of tHMGR and upc2-1 as well as methionine-repressible allele of ERG9 was grown in culture and amorphadiene production was measured for six days (FIG. 5). Limiting the FPP incorporated into squalene had a large impact on amorphadiene production, increasing it four-fold to 61 µg amorphadiene mL$^{-1}$ over the strain EPY209 containing the wild type ERG9 allele. Although limited in its ability to produce ergosterol, EPY212 still grew to a final OD ~75% of that of EPY209.

Overexpression of FPP Synthase. FPP Synthase (FPPS), encoded by ERG20, was targeted as the next target for overexpression in hopes of increasing sesquiterpene yields further. A six-fold increase in FPPS activity has been correlated with an 80% and 32% increase in dolichol and ergosterol, respectively (Szkopinska et al. (2000) Biochemical and Biophysical Research Communications, 267(1):473-477). Similar to the studies overexpressing HMGR and upc2-1, ERG20 was first cloned behind the GAL1 promoter on a high copy plasmid to create pRS-ERG20. Coexpression of ERG20 on this plasmid with pRS425ADS actually lowered the absolute productivity of amorphadiene by 60%. It is possible that an increase in FPPS activity increased only the content of other FPP derived products such as ergosterol. Another possibility is that overexpression of FPPS increased the intracellular concentration of FPPthe main signal for HMGR degradation (Gardner et al. (1999) J. Biol. Chem. 274(44):31671-31678). Without the overexpression of a deregulated form of the reductase, increased FPP concentrations could act to limit flux through the mevalonate pathway and decrease amorphadiene production.

pδ-ERG20 was then constructed for the integration and expression of ERG20 in our highest amorphadiene producer. The URA3 marker was recycled, and pδ-ERG20 integrated in the chromosome to create strain EPY212. This strain overexpressing FPPS, further increased the production of amorphadiene to 73 g amorphadiene mL$^{-1}$ (FIG. 5). Earlier we had seen a 60% decrease in amorphadiene production in strain EPY206 overexpressing ERG20 with ADS. However, now in a strain expressing tHMGR and upc2-1 and with a regulated squalene synthase, amorphadiene production increased 20% with the overexpression of ERG20.

In strains EPY206 and EPY212 each expressing ERG20, a decrease in cell density was observed. This decrease in cell growth might be explained by a toxicity caused directly by ERG20p. Alternatively an effect could arise from an accumulation or depletion of a pathway intermediate due to modified flux through the FPP synthase.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

---

What is claimed is:

1. A genetically modified eukaryotic host cell that produces an isoprenoid or an isoprenoid precursor compound via a mevalonate pathway, the genetically modified eukaryotic host cell comprising genetic modifications comprising:

a) a heterologous nucleic acid, integrated into the host cell's chromosome, encoding an enzyme that converts 3-hydroxy-3-methylglutaryl coenzyme-A (HMG-CoA) to mevalonate;

b) a heterologous nucleic acid, integrated into the host cell's chromosome, encoding a prenyl transferase;

c) a heterologous nucleic acid, integrated into the host cell's chromosome, to decrease the level of activity of squalene synthase; and d) a heterologous nucleic acid comprising a nucleotide sequence encoding a terpene synthase, wherein the genetic modifications provide for production of an isoprenoid or an isoprenoid precursor compound at a level that is at least about 50% higher than the level of the isoprenoid or isoprenoid precursor compound in a control cell not comprising the genetic modifications.

2. The genetically modified eukaryotic host cell of claim 1, wherein the genetically modified eukaryotic host cell is a yeast cell.

3. The genetically modified host cell of claim 2, wherein the genetically modified eukaryotic host cell is *Saccharomyces cerevisiae*.

4. The genetically modified host cell of claim 1, wherein the genetically modified host cell is genetically modified with a nucleic acid comprising a nucleotide sequence encoding enzyme that converts HMG-CoA to mevalonate is a truncated HMG-CoA reductase.

5. The genetically modified host cell of claim 1, wherein the genetically modified host cell is genetically modified with a nucleic acid comprising a nucleotide sequence encoding a variant Ecm22p transcription factor, which variant has increased transcriptional activation activity compared to wild-type Ecm22p, wherein the level of transcription of one or more mevalonate pathway enzymes is increased.

6. The genetically modified host cell of claim 5, wherein the level of transcription of hydroxymethylglutaryl coenzyme-A synthase, mevalonate kinase, and phosphomevalonate kinase is increased.

7. The genetically modified host cell of claim 1, wherein the genetically modified host cell is genetically modified with a nucleic acid comprising a nucleotide sequence encoding a variant Upc2p transcription factor, which variant has increased transcriptional activation activity compared to wild-type Upc2p, wherein the level of transcription of one or more mevalonate pathway enzymes is increased.

8. The genetically modified host cell of claim 7, wherein the level of transcription of hydroxymethylglutaryl coenzyme-A synthase, mevalonate kinase, and phosphomevalonate kinase is increased.

9. The genetically modified host cell of claim 1, wherein the genetically modified host cell is genetically modified with a nucleic acid comprising a heterologous promoter, which heterologous promoter replaces an endogenous promoter operably linked to an endogenous nucleotide sequence encoding squalene synthase, wherein the heterologous promoter provides for a reduced level of squalene synthase compared to a control host cell.

10. The genetically modified eukaryotic host cell of claim 1, wherein expression of the enzyme that converts HMG-CoA to mevalonate is under inducible control.

11. The genetically modified eukaryotic host cell of claim 1, wherein expression of the enzyme that converts HMG-CoA to mevalonate is under the control of a GAL1 promoter.

12. The genetically modified eukaryotic host cell of claim 1, wherein expression of the enzyme that converts HMG-CoA to mevalonate is under constitutive control.

13. The genetically modified eukaryotic host cell of claim 1, wherein expression of the prenyl transferase is under inducible control.

14. The genetically modified eukaryotic host cell of claim 13, wherein expression of the prenyl transferase is under the control of a GAL1 promoter.

15. The genetically modified eukaryotic host cell of claim 1, wherein expression of the prenyl transferase is under constitutive control.

16. The genetically modified host cell of claim 1, wherein the prenyl transferase is geranyl pyrophosphate synthase.

17. A method for enhancing production of an isoprenoid precursor or an isoprenoid via a mevalonate pathway in a host cell, the method comprising culturing the genetically modified eukaryotic host cell of claim 1 in a suitable medium and under conditions that promote production of the isoprenoid or isoprenoid precursor compound, wherein the isoprenoid or an isoprenoid precursor compound is produced at a level that is at least about 50% higher than the level of the isoprenoid or isoprenoid precursor compound in a control cell not comprising the genetic modifications.

18. The method of claim 17, wherein the conditions comprise inclusion in the culture medium of an inducing agent that activates an inducible promoter.

19. The method of claim 17, wherein the isoprenoid is a diterpene.

20. The method of claim 4, wherein the truncated HMG-CoA reductase comprises an amino acid sequence having at least 95% identity to the amino acid sequence set forth in SEQ ID NO:2.

21. The method of claim 5, wherein the variant Ecmp22 comprises substitution of glycine-to-aspartic acid substitution at amino acid 790.

* * * * *

SEQUENCE LISTING

```
<160> NUMBER OF SEQ ID NOS: 12

<210> SEQ ID NO 1
<211> LENGTH: 1509
<212> TYPE: DNA
<213> ORGANISM: Saccharomyces cerevisiae
<220> FEATURE:
<221> NAME/KEY: CDS
<222> LOCATION: (1)...(1509)

<400> SEQUENCE: 1 atg gtt tta acc aat aaa aca gtc att tct gga tcg aaa gtc aaa agt         48
Met Val Leu Thr Asn Lys Thr Val Ile Ser Gly Ser Lys Val Lys Ser
1               5                   10                  15 tta tca tct gcg caa tcg agc tca tca gga cct tca tca tct agt gag         96
Leu Ser Ser Ala Gln Ser Ser Ser Gly Pro Ser Ser Ser Ser Glu
                20                  25                  30 gaa gat gat tcc cgc gat att gaa agc ttg gat aag aaa ata cgt cct        144
Glu Asp Asp Ser Arg Asp Ile Glu Ser Leu Asp Lys Lys Ile Arg Pro
            35                  40                  45 tta gaa gaa tta gaa gca tta tta agt agt gga aat aca aaa caa ttg        192
Leu Glu Glu Leu Glu Ala Leu Leu Ser Ser Gly Asn Thr Lys Gln Leu
        50                  55                  60 aag aac aaa gag gtc gct gcc ttg gtt att cac ggt aag tta cct ttg        240
Lys Asn Lys Glu Val Ala Ala Leu Val Ile His Gly Lys Leu Pro Leu
65                  70                  75                  80 tac gct ttg gag aaa aaa tta ggt gat act acg aga gcg gtt gcg gta        288
Tyr Ala Leu Glu Lys Lys Leu Gly Asp Thr Thr Arg Ala Val Ala Val
                85                  90                  95 cgt agg aag gct ctt tca att ttg gca gaa gct cct gta tta gca tct        336
Arg Arg Lys Ala Leu Ser Ile Leu Ala Glu Ala Pro Val Leu Ala Ser
                100                 105                 110 gat cgt tta cca tat aaa aat tat gac tac gac cgc gta ttt ggc gct        384
Asp Arg Leu Pro Tyr Lys Asn Tyr Asp Tyr Asp Arg Val Phe Gly Ala
            115                 120                 125 tgt tgt gaa aat gtt ata ggt tac atg cct ttg ccc gtt ggt gtt ata        432
Cys Cys Glu Asn Val Ile Gly Tyr Met Pro Leu Pro Val Gly Val Ile
        130                 135                 140 ggc ccc ttg gtt atc gat ggt aca tct tat cat ata cca atg gca act        480
Gly Pro Leu Val Ile Asp Gly Thr Ser Tyr His Ile Pro Met Ala Thr
145                 150                 155                 160 aca gag ggt tgt ttg gta gct tct gcc atg cgt ggc tgt aag gca atc        528
Thr Glu Gly Cys Leu Val Ala Ser Ala Met Arg Gly Cys Lys Ala Ile
                165                 170                 175
```

```
aat gct ggc ggt ggt gca aca act gtt tta act aag gat ggt atg aca      576
Asn Ala Gly Gly Gly Ala Thr Thr Val Leu Thr Lys Asp Gly Met Thr
            180                 185                 190 aga ggc cca gta gtc cgt ttc cca act ttg aaa aga tct ggt gcc tgt      624
Arg Gly Pro Val Val Arg Phe Pro Thr Leu Lys Arg Ser Gly Ala Cys
        195                 200                 205 aag ata tgg tta gac tca gaa gag gga caa aac gca att aaa aaa gct      672
Lys Ile Trp Leu Asp Ser Glu Glu Gly Gln Asn Ala Ile Lys Lys Ala
    210                 215                 220 ttt aac tct aca tca aga ttt gca cgt ctg caa cat att caa act tgt      720
Phe Asn Ser Thr Ser Arg Phe Ala Arg Leu Gln His Ile Gln Thr Cys
225                 230                 235                 240 cta gca gga gat tta ctc ttc atg aga ttt aga aca act act ggt gac      768
Leu Ala Gly Asp Leu Leu Phe Met Arg Phe Arg Thr Thr Thr Gly Asp
                245                 250                 255 gca atg ggt atg aat atg att tct aaa ggt gtc gaa tac tca tta aag      816
Ala Met Gly Met Asn Met Ile Ser Lys Gly Val Glu Tyr Ser Leu Lys
            260                 265                 270 caa atg gta gaa gag tat ggc tgg gaa gat atg gag gtt gtc tcc gtt      864
Gln Met Val Glu Glu Tyr Gly Trp Glu Asp Met Glu Val Val Ser Val
        275                 280                 285 tct ggt aac tac tgt acc gac aaa aaa cca gct gcc atc aac tgg atc      912
Ser Gly Asn Tyr Cys Thr Asp Lys Lys Pro Ala Ala Ile Asn Trp Ile
    290                 295                 300 gaa ggt cgt ggt aag agt gtc gtc gca gaa gct act att cct ggt gat      960
Glu Gly Arg Gly Lys Ser Val Val Ala Glu Ala Thr Ile Pro Gly Asp
305                 310                 315                 320 gtt gtc aga aaa gtg tta aaa agt gat gtt tcc gca ttg gtt gag ttg     1008
Val Val Arg Lys Val Leu Lys Ser Asp Val Ser Ala Leu Val Glu Leu
                325                 330                 335 aac att gct aag aat ttg gtt gga tct gca atg gct ggg tct gtt ggt     1056
Asn Ile Ala Lys Asn Leu Val Gly Ser Ala Met Ala Gly Ser Val Gly
            340                 345                 350 gga ttt aac gca cat gca gct aat tta gtg aca gct gtt ttc ttg gca     1104
Gly Phe Asn Ala His Ala Ala Asn Leu Val Thr Ala Val Phe Leu Ala
        355                 360                 365 tta gga caa gat cct gca caa aat gtt gaa agt tcc aac tgt ata aca     1152
Leu Gly Gln Asp Pro Ala Gln Asn Val Glu Ser Ser Asn Cys Ile Thr
    370                 375                 380 ttg atg aaa gaa gtg gac ggt gat ttg aga att tcc gta tcc atg cca     1200
Leu Met Lys Glu Val Asp Gly Asp Leu Arg Ile Ser Val Ser Met Pro
385                 390                 395                 400 tcc atc gaa gta ggt acc atc ggt ggt ggt act gtt cta gaa cca caa     1248
Ser Ile Glu Val Gly Thr Ile Gly Gly Gly Thr Val Leu Glu Pro Gln
                405                 410                 415 ggt gcc atg ttg gac tta tta ggt gta aga ggc ccg cat gct acc gct     1296
Gly Ala Met Leu Asp Leu Leu Gly Val Arg Gly Pro His Ala Thr Ala
            420                 425                 430 cct ggt acc aac gca cgt caa tta gca aga ata gtt gcc tgt gcc gtc     1344
Pro Gly Thr Asn Ala Arg Gln Leu Ala Arg Ile Val Ala Cys Ala Val
        435                 440                 445 ttg gca ggt gaa tta tcc tta tgt gct gcc cta gca gcc ggc cat ttg     1392
Leu Ala Gly Glu Leu Ser Leu Cys Ala Ala Leu Ala Ala Gly His Leu
    450                 455                 460 gtt caa agt cat atg acc cac aac agg aaa cct gct gaa cca aca aaa     1440
Val Gln Ser His Met Thr His Asn Arg Lys Pro Ala Glu Pro Thr Lys
465                 470                 475                 480 cct aac aat ttg gac gcc act gat ata aat cgt ttg aaa gat ggg tcc     1488
Pro Asn Asn Leu Asp Ala Thr Asp Ile Asn Arg Leu Lys Asp Gly Ser
```

-continued

```
               485              490              495
gtc acc tgc att aaa tcc taa                                        1509
Val Thr Cys Ile Lys Ser *
            500
```

<210> SEQ ID NO 2
<211> LENGTH: 502
<212> TYPE: PRT
<213> ORGANISM: Saccharomyces cerevisiae

<400> SEQUENCE: 2

```
Met Val Leu Thr Asn Lys Thr Val Ile Ser Gly Ser Lys Val Lys Ser
1               5                   10                  15

Leu Ser Ser Ala Gln Ser Ser Ser Gly Pro Ser Ser Ser Ser Ser Glu
            20                  25                  30

Glu Asp Asp Ser Arg Asp Ile Glu Ser Leu Asp Lys Lys Ile Arg Pro
        35                  40                  45

Leu Glu Glu Leu Glu Ala Leu Leu Ser Ser Gly Asn Thr Lys Gln Leu
    50                  55                  60

Lys Asn Lys Glu Val Ala Ala Leu Val Ile His Gly Lys Leu Pro Leu
65                  70                  75                  80

Tyr Ala Leu Glu Lys Lys Leu Gly Asp Thr Thr Arg Ala Val Ala Val
                85                  90                  95

Arg Arg Lys Ala Leu Ser Ile Leu Ala Glu Ala Pro Val Leu Ala Ser
            100                 105                 110

Asp Arg Leu Pro Tyr Lys Asn Tyr Asp Tyr Asp Arg Val Phe Gly Ala
        115                 120                 125

Cys Cys Glu Asn Val Ile Gly Tyr Met Pro Leu Pro Val Gly Val Ile
    130                 135                 140

Gly Pro Leu Val Ile Asp Gly Thr Ser Tyr His Ile Pro Met Ala Thr
145                 150                 155                 160

Thr Glu Gly Cys Leu Val Ala Ser Ala Met Arg Gly Cys Lys Ala Ile
                165                 170                 175

Asn Ala Gly Gly Gly Ala Thr Thr Val Leu Thr Lys Asp Gly Met Thr
            180                 185                 190

Arg Gly Pro Val Val Arg Phe Pro Thr Leu Lys Arg Ser Gly Ala Cys
        195                 200                 205

Lys Ile Trp Leu Asp Ser Glu Glu Gly Gln Asn Ala Ile Lys Lys Ala
    210                 215                 220

Phe Asn Ser Thr Ser Arg Phe Ala Arg Leu Gln His Ile Gln Thr Cys
225                 230                 235                 240

Leu Ala Gly Asp Leu Leu Phe Met Arg Phe Arg Thr Thr Thr Gly Asp
                245                 250                 255

Ala Met Gly Met Asn Met Ile Ser Lys Gly Val Glu Tyr Ser Leu Lys
            260                 265                 270

Gln Met Val Glu Glu Tyr Gly Trp Glu Asp Met Glu Val Val Ser Val
        275                 280                 285

Ser Gly Asn Tyr Cys Thr Asp Lys Lys Pro Ala Ala Ile Asn Trp Ile
    290                 295                 300

Glu Gly Arg Gly Lys Ser Val Val Ala Glu Ala Thr Ile Pro Gly Asp
305                 310                 315                 320

Val Val Arg Lys Val Leu Lys Ser Asp Val Ser Ala Leu Val Glu Leu
                325                 330                 335

Asn Ile Ala Lys Asn Leu Val Gly Ser Ala Met Ala Gly Ser Val Gly
            340                 345                 350
```

Gly Phe Asn Ala His Ala Ala Asn Leu Val Thr Ala Val Phe Leu Ala
            355                 360                 365

Leu Gly Gln Asp Pro Ala Gln Asn Val Glu Ser Ser Asn Cys Ile Thr
    370                 375                 380

Leu Met Lys Glu Val Asp Gly Asp Leu Arg Ile Ser Val Ser Met Pro
385                 390                 395                 400

Ser Ile Glu Val Gly Thr Ile Gly Gly Thr Val Leu Glu Pro Gln
                405                 410                 415

Gly Ala Met Leu Asp Leu Leu Gly Val Arg Gly Pro His Ala Thr Ala
            420                 425                 430

Pro Gly Thr Asn Ala Arg Gln Leu Ala Arg Ile Val Ala Cys Ala Val
            435                 440                 445

Leu Ala Gly Glu Leu Ser Leu Cys Ala Ala Leu Ala Ala Gly His Leu
    450                 455                 460

Val Gln Ser His Met Thr His Asn Arg Lys Pro Ala Glu Pro Thr Lys
465                 470                 475                 480

Pro Asn Asn Leu Asp Ala Thr Asp Ile Asn Arg Leu Lys Asp Gly Ser
                485                 490                 495

Val Thr Cys Ile Lys Ser
            500

<210> SEQ ID NO 3
<211> LENGTH: 32
<212> TYPE: DNA
<213> ORGANISM: Artificial Sequence
<220> FEATURE:
<223> OTHER INFORMATION: Primer

<400> SEQUENCE: 3
ggactagtaa aacaatggcc ctgaccgaag ag                                32

<210> SEQ ID NO 4
<211> LENGTH: 29
<212> TYPE: DNA
<213> ORGANISM: Artificial Sequence
<220> FEATURE:
<223> OTHER INFORMATION: Primer

<400> SEQUENCE: 4
ccaagctttc agatggacat cgggtaaac                                   29

<210> SEQ ID NO 5
<211> LENGTH: 35
<212> TYPE: DNA
<213> ORGANISM: Artificial Sequence
<220> FEATURE:
<223> OTHER INFORMATION: Primer

<400> SEQUENCE: 5
cgggatccaa aacaatggct gcagaccaat tggtg                            35

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
gcgtcgactt aggatttaat gcaggtgacg                                  30

```
<210> SEQ ID NO 7
<211> LENGTH: 29
<212> TYPE: DNA
<213> ORGANISM: Artificial Sequence
<220> FEATURE:
<223> OTHER INFORMATION: Primer

<400> SEQUENCE: 7
ctgccgcggg gccgcaaatt aaagccttc                                    29

<210> SEQ ID NO 8
<211> LENGTH: 29
<212> TYPE: DNA
<213> ORGANISM: Artificial Sequence
<220> FEATURE:
<223> OTHER INFORMATION: Primer

<400> SEQUENCE: 8
ctgccgcggt agtacggatt agaagccgc                                    29

<210> SEQ ID NO 9
<211> LENGTH: 35
<212> TYPE: DNA
<213> ORGANISM: Artificial Sequence
<220> FEATURE:
<223> OTHER INFORMATION: Primer

<400> SEQUENCE: 9
cgggatccaa aacaatgagc gaagtcggta tacag                             35

<210> SEQ ID NO 10
<211> LENGTH: 34
<212> TYPE: DNA
<213> ORGANISM: Artificial Sequence
<220> FEATURE:
<223> OTHER INFORMATION: Primer

<400> SEQUENCE: 10
gcgtcgactc ataacgaaaa atcagagaaa tttg                              34

<210> SEQ ID NO 11
<211> LENGTH: 36
<212> TYPE: DNA
<213> ORGANISM: Artificial Sequence
<220> FEATURE:
<223> OTHER INFORMATION: Primer

<400> SEQUENCE: 11
cgggatccaa aacaatgaca tccgatgatg ggaatg                            36

<210> SEQ ID NO 12
<211> LENGTH: 34
<212> TYPE: DNA
<213> ORGANISM: Artificial Sequence
<220> FEATURE:
<223> OTHER INFORMATION: Primer

<400> SEQUENCE: 12
gcgtcgactt acataaaagc tgaaaagttt gtag                              34
```